United States Patent
Honaryar et al.

(10) Patent No.: US 9,028,394 B2
(45) Date of Patent: May 12, 2015

(54) SELF-ADJUSTING MECHANICAL GASTRIC BAND

(75) Inventors: Babak Honaryar, Orinda, CA (US);
Marcos Borrell, Goleta, CA (US);
Philip Bryer, Tarzana, CA (US); Robert E. Hoyt, Santa Barbara, CA (US);
Joseph Raven, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 461 days.

(21) Appl. No.: 12/770,640

(22) Filed: Apr. 29, 2010

(65) Prior Publication Data

US 2011/0270018 A1 Nov. 3, 2011

(51) Int. Cl.
*A61F 2/00* (2006.01)
*A61F 13/00* (2006.01)
*A61F 5/00* (2006.01)

(52) U.S. Cl.
CPC ...................................... *A61F 5/005* (2013.01)

(58) Field of Classification Search
CPC ..... A61F 5/005; A61F 5/0053; A61F 5/0056; A61F 5/0059; A61F 5/0063
USPC .............. 600/29–31, 37; 623/14.13; 606/153, 606/157, 191, 192, 201–203; 604/19, 604/99.01, 96.01
See application file for complete search history.

(56) References Cited

U.S. PATENT DOCUMENTS

| | | | |
|---|---|---|---|
| 1,174,814 A | 3/1916 | Brennan et al. | |
| 1,830,947 A | 11/1931 | Klingel | |
| 1,999,683 A | 4/1935 | Borresen | |
| 2,163,048 A | 6/1939 | McKee | |
| 2,339,138 A | 1/1944 | Black | |
| 2,405,667 A | 8/1946 | Ottesen | |
| 2,438,231 A | 3/1948 | Schultz et al. | |
| 2,635,907 A | 4/1953 | Heimbuch | |
| 2,714,469 A | 8/1955 | Carlson | |
| 2,936,980 A | 5/1960 | Rapata | |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

"Innovative medical devices and implants"; LGSP medical futures, p. 5.

(Continued)

*Primary Examiner* — Jacqueline Cheng
*Assistant Examiner* — Eileen Hyde
(74) *Attorney, Agent, or Firm* — Gordon & Jacobson, PC

(57) ABSTRACT

A self-adjusting gastric band applies a substantially constant force to a patient's fundus in order to facilitate weight control. The self-adjusting gastric band is capable of automatically relaxing and contracting in response to changes in the patient's fundus or in response to a large bolus passing through the patient's fundus that is constricted by the gastric band. The self-adjusting gastric band is automatically adjustable without hydraulic fluid and without external physician intervention. The self-adjusting gastric band comprises a movable member and a biasing mechanism coupled to the movable member to facilitate applying the substantially constant force against the fundus as the fundus changes size, shape and/or position.

30 Claims, 14 Drawing Sheets

(56) References Cited

U.S. PATENT DOCUMENTS

| | | |
|---|---|---|
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | de Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,265,890 A * | 11/1993 | Balsells ............... 277/467 |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdile et al. |
| 6,383,219 B1 | 5/2002 | Telandro et al. |
| 6,387,105 B1 | 5/2002 | Gifford, III et al. |
| 6,417,750 B1 | 7/2002 | Sohn |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |

(56) References Cited

U.S. PATENT DOCUMENTS

| | | |
|---|---|---|
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 * | 4/2003 | Dargent et al. ............... 606/157 |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredericks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fischer et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |

(56) References Cited

U.S. PATENT DOCUMENTS

| | | |
|---|---|---|
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0082793 A1 | 4/2005 | Lee |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1* | 9/2005 | Birk .................. 604/96.01 |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1* | 7/2006 | Hassler et al. ............... 606/153 |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1* | 12/2006 | Hill et al. .................. 606/157 |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097487 A1* | 4/2008 | Pool et al. .................. 606/151 |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |

(56) References Cited

U.S. PATENT DOCUMENTS

| | | |
|---|---|---|
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 * | 7/2009 | Coe et al. ............ 606/157 |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0240228 A1 * | 9/2010 | Lenhert ............ 439/32 |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |

FOREIGN PATENT DOCUMENTS

| | | | |
|---|---|---|---|
| CN | 1367670 | 9/2002 | |
| DE | 10020688 | 12/2000 | |
| EP | 0119596 | 9/1984 | |
| EP | 0230747 | 8/1987 | |
| EP | 0416250 | 3/1991 | |
| EP | 0611561 | 8/1994 | |
| EP | 0695558 | 2/1996 | |
| EP | 0876808 | 11/1998 | |
| EP | 1036545 | 9/2000 | |
| EP | 1072282 | 1/2001 | |
| EP | 1105073 | 6/2001 | |
| EP | 1396242 | 3/2004 | |
| EP | 1396243 | 3/2004 | |
| EP | 1491167 | 12/2004 | |
| EP | 1491168 | 12/2004 | |
| EP | 1529502 | 5/2005 | |
| EP | 1547549 | 6/2005 | |
| EP | 1547549 A2 * | 6/2005 | ............ A61F 5/00 |
| EP | 1574189 | 9/2005 | |
| EP | 1600183 | 11/2005 | |
| EP | 1602346 | 12/2005 | |
| EP | 1704833 | 9/2006 | |
| EP | 1719480 | 11/2006 | |
| EP | 1736123 | 12/2006 | |
| EP | 1736195 | 12/2006 | |
| EP | 1736202 | 12/2006 | |
| EP | 1743605 | 1/2007 | |
| EP | 1829504 | 9/2007 | |
| EP | 1829505 | 9/2007 | |
| EP | 1829506 | 9/2007 | |
| EP | 1967168 | 9/2008 | |
| EP | 1992315 | 11/2008 | |
| EP | 2074970 | 7/2009 | |
| EP | 2074971 | 7/2009 | |
| EP | 2074972 | 7/2009 | |
| EP | 2095796 | 9/2009 | |
| EP | 2095798 | 9/2009 | |
| EP | 2191796 | 6/2010 | |
| FR | 2688693 | 9/1993 | |
| FR | 2769491 | 4/1999 | |
| FR | 2783153 | 3/2000 | |
| FR | 2797181 | 2/2001 | |
| FR | 2799118 | 4/2001 | |
| FR | 2823663 | 10/2002 | |
| FR | 2921822 | 4/2009 | |
| GB | 1174814 | 12/1969 | |
| GB | 2090747 | 7/1982 | |
| JP | 57-171676 | 10/1982 | |
| JP | 2-019147 | 1/1990 | |
| JP | 11-244395 | 9/1999 | |
| JP | 2003-526410 | 9/2003 | |
| JP | 2005-131380 | 5/2005 | |
| JP | 2005-334658 | 12/2005 | |
| WO | WO 86/00079 | 1/1986 | |
| WO | WO 86/00912 | 2/1986 | |
| WO | WO 89/11701 | 11/1989 | |
| WO | WO 90/00369 | 1/1990 | |
| WO | WO 92/20349 | 11/1992 | |
| WO | WO 94/02517 | 2/1994 | |
| WO | WO 96/33751 | 1/1996 | |
| WO | WO 98/35639 | 8/1998 | |
| WO | WO 98/35640 | 8/1998 | |
| WO | WO 00/00108 | 1/2000 | |
| WO | WO 00/01428 | 1/2000 | |
| WO | WO 00/09047 | 2/2000 | |
| WO | WO 00/09049 | 2/2000 | |
| WO | WO 00/15158 | 3/2000 | |
| WO | WO 00/66196 | 11/2000 | |
| WO | WO 01/10359 | 2/2001 | |
| WO | WO 01/12078 | 2/2001 | |
| WO | WO 01/41671 | 6/2001 | |
| WO | WO 01/47435 | 7/2001 | |
| WO | WO 01/47575 | 7/2001 | |
| WO | WO 01/49245 | 7/2001 | |
| WO | WO 01/52777 | 7/2001 | |
| WO | WO 01/68007 | 9/2001 | |
| WO | WO 01/85071 | 11/2001 | |
| WO | WO 02/05753 | 1/2002 | |
| WO | WO 02/09792 | 2/2002 | |
| WO | WO 02/19953 | 3/2002 | |
| WO | WO 02/26317 | 4/2002 | |
| WO | WO 02/053093 | 7/2002 | |
| WO | WO 02/065948 | 8/2002 | |
| WO | WO 02/096326 | 12/2002 | |
| WO | WO 03/007782 | 1/2003 | |
| WO | 03057092 A2 | 7/2003 | |
| WO | WO 03/055420 | 7/2003 | |
| WO | WO 03/057092 | 7/2003 | |
| WO | WO 03/059215 | 7/2003 | |
| WO | WO 03/077191 | 9/2003 | |
| WO | WO 03/101352 | 12/2003 | |
| WO | WO 03/105732 | 12/2003 | |
| WO | WO 2004/014245 | 2/2004 | |

(56) References Cited

FOREIGN PATENT DOCUMENTS

| | | |
|---|---|---|
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 7/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Corporation, an Inamed Company, BioEnterics Intragastric Balloon; Directions for Use Published Document, P/N 94200 Rev: B, pp. 1-56.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 The European Asociation for Cardio-thoracic Surgery; 1 page.
Cummings et al.; "Plasma Ghrelin Levels After Diet-Induced Weight Loss or Gastric Bypass Sugery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide Yy Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.

(56) References Cited

OTHER PUBLICATIONS

Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V.13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: a Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Silver et al.; "Physical Properties of Hyaluronic Acid and Hydroxypropylmethylcellulose in Solution: Evaluation of Coating Ability" Journal of Applied Biomaterials, V. 5; pp. 89-98; 1994.
Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptidel secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "Y4 Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.
Brown et al; "Symmetrical Pouch Dilation After Laparoscopic Adjustable Gastric Banding: Incidence and Management"; Obesity Surgery; V. 18, pp. 1104-1108; 2008.
Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Helioscopie Product Insert for Heliogast, pp. 1-11 (undated).
Neary et al.; "Peptide YY(3-36) and Glucagon-Like Peptide-$1_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Patient Management After Lap-Band Placement; http://www.core.monash.org/patient-care.pdf.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
The Lap-Band Device & How it Works; http://lapband.com/en/learn_about-lapband/device_how_it_works/.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

\* cited by examiner

SELF-ADJUSTING MECHANICAL GASTRIC BAND

FIELD

The present invention generally relates to medical systems and apparatus and uses thereof for treating obesity and/or obesity-related diseases, and more specifically, relates to a gastric band that is self-adjusting.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the fundus, or esophageal junction, of a patient's upper stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Existing gastric bands periodically require adjustments to maintain an effective constriction about the fundus, to account for changes in the fundus tissue, reduction of fat or other factors causing movement and/or size change of the fundus. Some attempts have been made to allow for such adjustment of gastric bands. For example, hydraulic gastric bands utilize a fluid such as saline to fill an inflatable portion of the gastric band using a subcutaneous injection port. Adjustments to the amount of inflation may be made by injecting or extracting the fluid through the patient's skin into or out of the injection port, which then directs the fluid into or out of the inflatable portion of the gastric band. These types of adjustments may be undesirable because of the discomfort caused by the injections.

Further, adjustments by injections may not be immediately available when immediate adjustments may be desirable. For example, during normal operation of the gastric band, the band applies pressure to the outer surface of the fundus. But in some instances, the patient may swallow a bolus of food that is too large to pass through the constriction produced by the band. The result can be a painful experience which, if it persists, may require medical intervention to release the blockage.

Accordingly, it is desirable to develop a self-adjusting gastric band that will provide the needed pressure to the fundus to create the stoma and facilitate weight control, but that will also automatically self-adjust to account for changes in the fundus and/or to open up to allow a large bolus to pass through. It is further desirable to create an automatic, self-adjusting gastric band that does not require an electrical power source and/or external adjustments, to allow a large bolus to pass through, so that immediate relief from the discomfort created by a large bolus may be relieved. Moreover, it is desirable to develop a mechanically self-adjusting gastric band that does not require hydraulic adjustments through a subcutaneous injection port.

SUMMARY

Generally described herein are self-adjusting, mechanical gastric bands that apply a substantially constant force to a patient's fundus in order to facilitate weight control. Such self-adjusting gastric bands are capable of automatically relaxing and contracting in response changes in the patient's fundus or in response to a large bolus passing through the patient's fundus that is constricted by the gastric band. Furthermore, the self-adjusting gastric bands disclosed herein are automatically adjustable without hydraulic fluid.

Although certain embodiments of self-adjusting gastric bands are disclosed herein, it should be understood that the present invention contemplates any gastric band that is mechanically self-adjustable and that applies a substantially constant force to the fundus. The substantially constant force may have a target force in the range of approximately 0.05 to 1.0 lbf. However, the force variation from a first position and a second position in the gastric band may be less than approximately fifty percent. For example, for a band with a target force of 0.4 lbf, the variation in force between the two positions may be approximately 0.2 to 0.6 lbf, or 0.4+/−0.2 lbf.

In various embodiments, a self-adjusting gastric band may impose a range of constrictions on a fundus to accommodate changes in shape, size, and/or position of the fundus. For simplicity, a first constriction and a second constriction on the fundus in response to a first position and second position of the fundus may be referred to herein. However, it should be understood that various numbers of different constrictions are contemplated within the scope of the present invention, and that the range of constrictions may be a continuous range of constrictions.

In various embodiments, the range of constrictions may be described as ranges of inside diameters of the gastric band. The inside diameter of the band changes to provide a greater or lesser degree of constriction of the fundus. The inside diameter of the gastric band may change by an amount between approximately one-sixteenth of an inch and approximately one-half of an inch.

The self-adjusting gastric band comprises a movable member and a biasing mechanism coupled to the movable member to facilitate applying the substantially constant force against the fundus when the fundus is in the first position and the second position. The self-adjusting band applies the first constriction to the fundus when the fundus is in the first position. The band applies the second constriction to the fundus when the fundus is in the second position. The movable member self-adjusts as the fundus moves from the first position to the second position, and the biasing mechanism automatically moves the movable member with the substantially constant force as the fundus moves from the first position to the second position.

In an embodiment, the fundus moves from the first position to the second position as a large bolus enters the fundus. To allow the large bolus to pass through the fundus, the self-adjusting gastric band automatically moves from the first constriction to the second constriction, with the second constriction being looser than the first constriction. After the bolus passes through the fundus, the biasing mechanism automatically returns the movable member to the first constriction.

Further, in an embodiment, the movable member is a lobe comprising a rolling diaphragm coupled to a ring of the gastric band, and the biasing mechanism is a compression spring with substantially constant force in the range of operation. The near-constant force compression spring is disposed within a cup proximate the rolling diaphragm, and the spring abuts the ring to facilitate moving the rolling diaphragm to impose the first constriction and the second constriction on the fundus. The cup is slidably coupled to the ring and comprises a tab to prevent the near-constant force compression spring from expanding beyond a predetermined distance. A near-constant force compression spring may be achieved by choosing a spring with a low spring constant (K) and then pre-loading the spring to a desired target force by using a substantial portion of the range of deflection of the spring, leaving sufficient remaining deflection to accommodate a desired operation range of the gastric band.

In accordance with another embodiment, the movable member is a vertical cup slidably coupled to a roller that is coupled to a ring of the self-adjusting gastric band. The vertical cup is circumferentially disposed around the inside of a ring of the gastric band. The biasing mechanism is a torsional spring coupled to the roller. The torsional spring comprises ends that contact a back support of the ring to facilitate applying the substantially constant force to the vertical cup and the fundus. A moment arm of the torsional spring increases as the vertical cup slides toward the back support, and the increased moment arm facilitates maintaining the substantially constant force against the fundus.

Additionally, the self-adjusting gastric band comprises a retaining ring circumferentially disposed about the self-adjusting gastric band. The retaining ring comprising a release tab abutting a tab on the spring holder, which maintains the spring holder in a preloaded position against the back support. When the retaining ring rotates around the self-adjusting gastric band, the release tab slides past the spring holder tab to release the spring holder and the vertical cup. When released, the vertical cup exerts the substantially constant force on the fundus.

According to an embodiment, the self-adjusting gastric band comprises a latch mechanism that has a male portion and a female portion. The male portion comprises a cam screw and the female portion comprises a slidable cylinder. The cam screw comprises pins and the slidable cylinder comprises pin slots for receiving the pins when the cam screw is inserted into the slidable cylinder.

Further, the slidable cylinder comprises a tab that abuts a retaining ring release tab on the retaining ring. When the cam screw is inserted into the slidable cylinder and slides the slidable cylinder within the female portion, the cylinder tab pushes the retaining ring release tab to rotate the retaining ring. The retaining ring releases the vertical cup as the retaining ring rotates.

In accordance with another embodiment the movable member of the self-adjusting gastric band is a rotatable finger coupled to a pivot on a ring of the self-adjusting gastric band. The rotatable finger rotates counter-clockwise to apply the first constriction, and it rotates clockwise to apply the second constriction, for example, in response to the large bolus entering the fundus. The biasing mechanism is a leaf spring coupled to the ring, and the leaf spring biases the rotatable finger toward the fundus at the substantially constant force. A lever arm of the leaf spring increases as the rotatable finger rotates to the second constriction in order to maintain the substantially constant force.

DETAILED DESCRIPTION

Figure 1A:
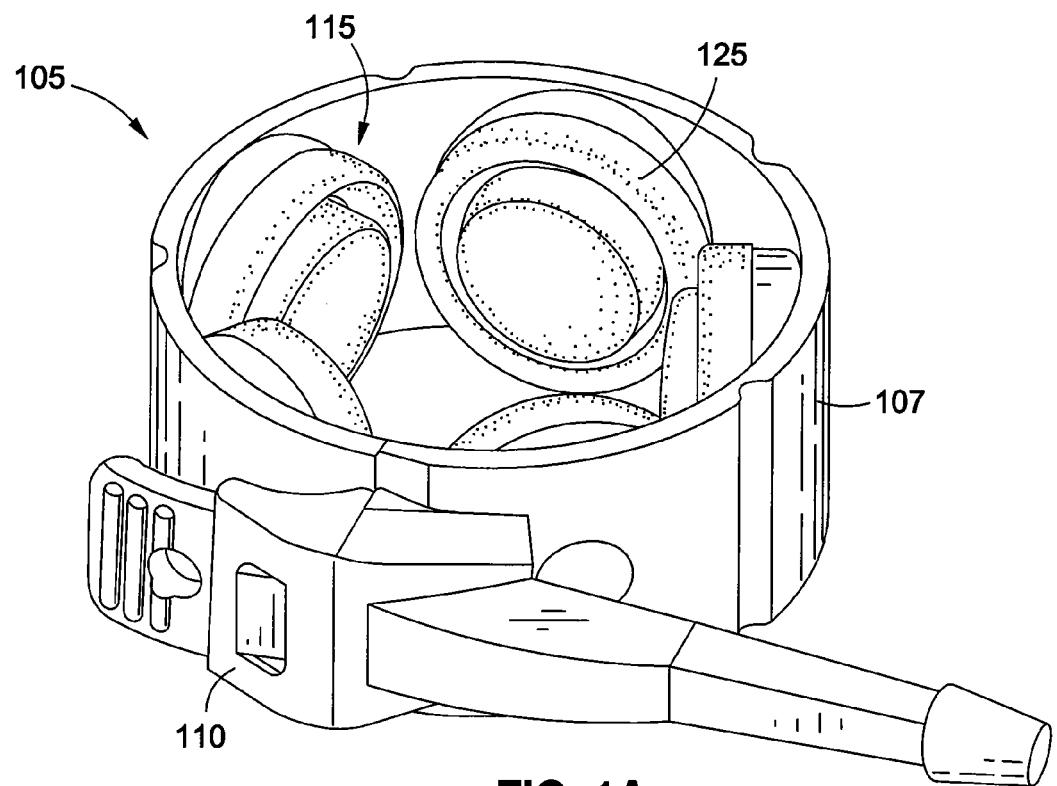
FIG. 1A illustrates a perspective view of a self-adjusting gastric band with circular lobes according to an embodiment of the present invention.
Figure 1B:
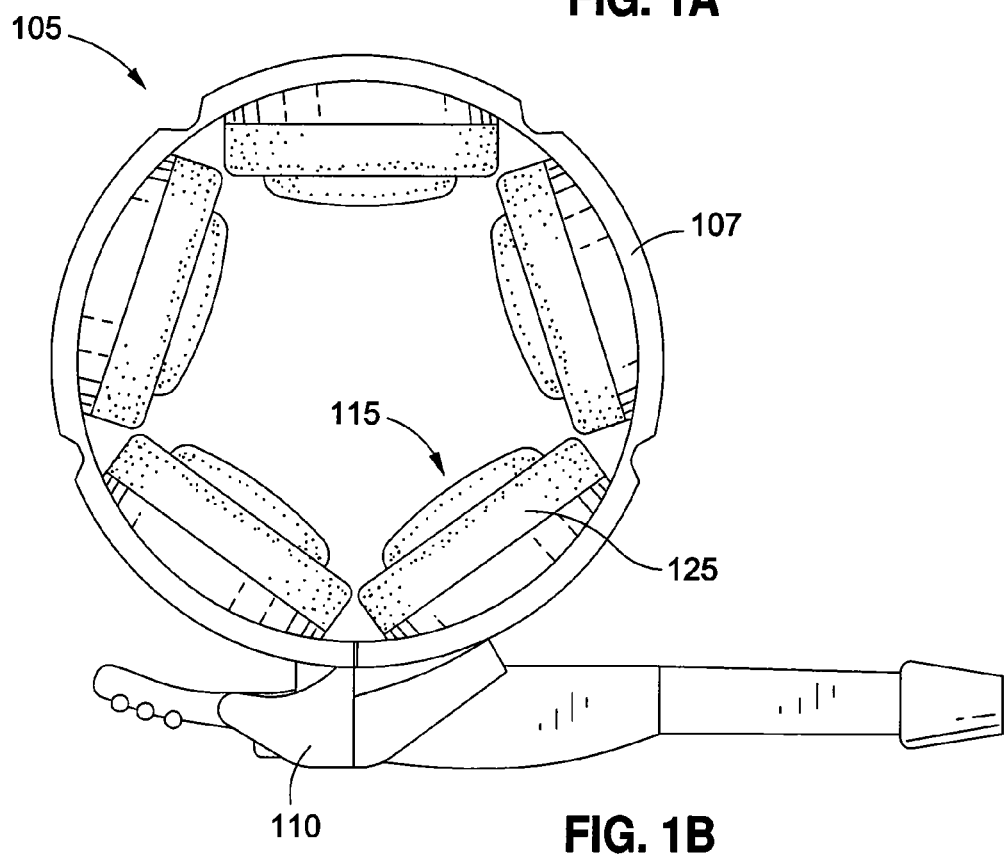
FIG. 1B illustrates a top view of the self-adjusting gastric band of FIG. 1A.

The present invention generally provides mechanically self-adjusting gastric banding systems, for example, for treatment of obesity and obesity related conditions, as well as systems for automatically controlling adjustment of gastric bands in response to changes in the patient's fundus or in response to a patient swallowing a large bolus.

Adjustable gastric bands are effective in helping a patient lose weight when the band is properly tightened around the patient's fundus, or esophageal junction. During normal operation, the band applies pressure to the outer surface of the fundus. But, in some instances, the size and/or shape of the fundus may change, or the patient may swallow a bolus which is too large to pass through the constriction produced by the band—for example, when the patient swallows a large piece of steak. The result can be a painful experience which, if it persists, may require medical intervention to release the blockage. In either case, adjustment of the gastric band may be necessary.

In accordance with various embodiments of the present invention, the mechanically self-adjusting gastric band provides a substantially constant force to the fundus to encourage weight loss. This substantially constant force is maintained even when the size and/or shape of the fundus changes, or when a large bolus of food is swallowed. It should be noted that the force is referred to herein as substantially constant, but it should be understood that embodiments disclosed herein function when the force is constant, and not just substantially constant.

The biasing mechanisms in the self-adjusting gastric band cause a movable member to move with the changing size of the fundus while maintaining the substantially constant force against the fundus. For example, the self-adjusting gastric band may temporarily and automatically open up to allow a large bolus to pass through the fundus. After the bolus passes through, the biasing mechanisms and movable members of the band return the band to its original constriction about the fundus. In various embodiments, the band is automatically self-adjusting and does not require manual and/or external adjustments in order to maintain the substantially constant pressure against the fundus.

As noted previously, certain embodiments of a mechanically self-adjusting gastric band will be disclosed herein. However, other configurations that allow for automatic, mechanical, self-adjusting gastric bands that apply a substantially constant force to the fundus are contemplated within the scope of the present invention. Thus the embodiments described below are only representative of the invention, and are not limiting.

With reference to FIGS. 1A-1E, a self-adjusting gastric band 105 comprises a plurality of movable members, or lobes 115 that apply a substantially constant pressure to a patient's fundus as the fundus changes in size, shape, and/or position. The gastric band 105 is configured to wrap around the patient's fundus such that the lobes 115 are circumferentially spaced about the fundus.

A latch mechanism 110 secures the band 105 in place around the fundus. The components of the latch mechanism 110 are located at the ends of a flexible, rigid ring 107 that forms the outside of the band 105 when it is wrapped around the fundus. In an embodiment, the outside diameter of the ring 107 is approximately two inches and the inside diameter is approximately one inch. The ring 107 provides structure and support to the band 105, and may be constructed of molded silicone rubber with a shore A durometer in the range of approximately 50-60. FIG. 1E illustrates the band 105 with the ring open prior to being implanted around the fundus in accordance with an embodiment. In an embodiment, hinges may be located between the lobes 115 to allow the ring 107 to open and/or close around the fundus. For example, living hinges may be located between the lobes 115.

Figure 1C:
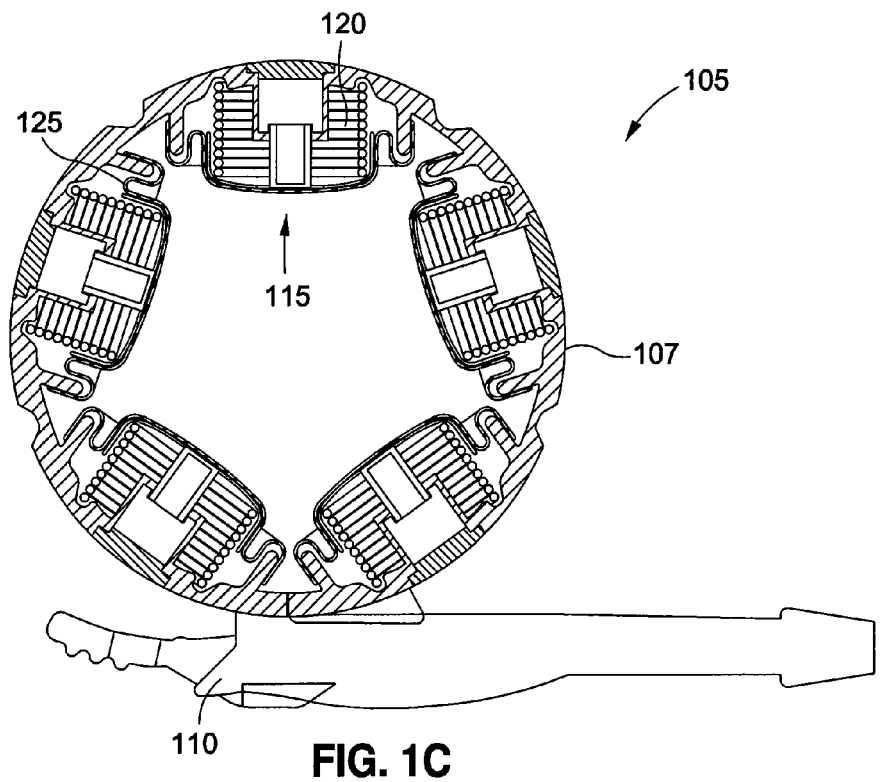
FIG. 1C illustrates a top, cross-sectional view of the self-adjusting gastric band of FIG. 1A.
Figure 1D:
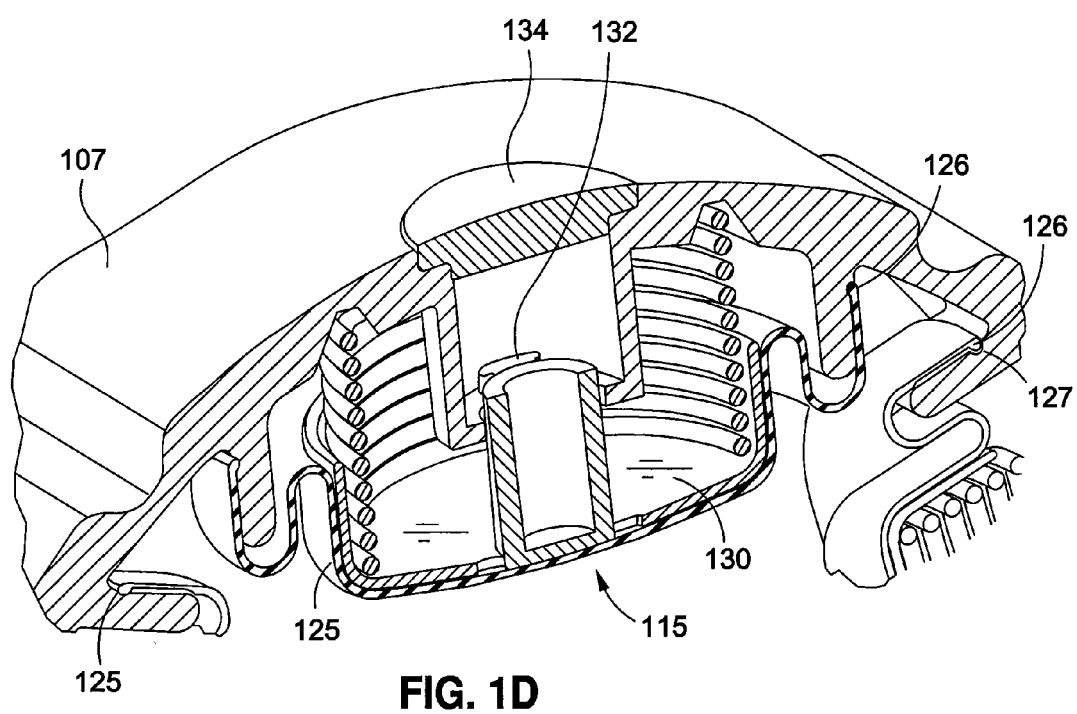
FIG. 1D illustrates a perspective, sectional view of the self-adjusting gastric band of FIG. 1A.
Figure 1E:
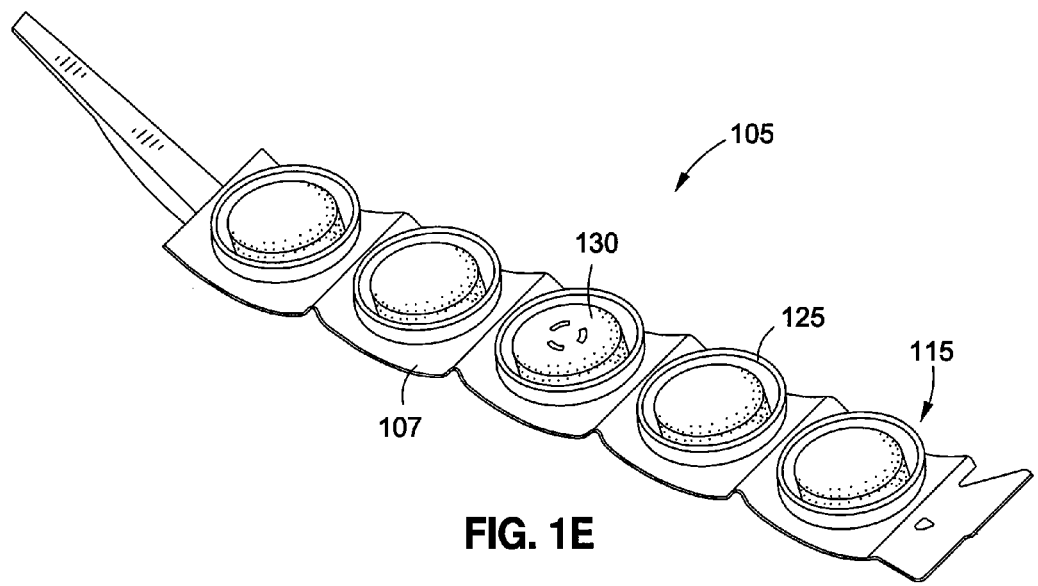
FIG. 1E illustrates a perspective view of an unlatched, self-adjusting gastric band, with a rolling diaphragm shown transparently to illustrate a spring cup according to an embodiment of the present invention.

With reference to FIGS. 1C-1D, in an embodiment, the lobes 115 move in and out to accommodate changes in size, shape, and/or location of the fundus, for example, to allow a large bolus of food to pass through the fundus. The lobes 115 apply a substantially constant pressure to the fundus via biasing mechanisms, such as compression springs 120, located in the lobes 115.

The compression springs may be made of stainless steel, titanium, or any other material that provides a sufficient force with a low enough k-value to facilitate applying a substantially constant force to the fundus with the lobes 115. In an embodiment, the compression springs 120 undergo a large deflection when they are loaded into the lobes 115. In this manner, small changes in the compression of the springs 120 have little or substantially no effect on the force exerted by the springs 120, resulting in a substantially constant force applied by the springs 120 and the lobes 115 in response to deflections due to fundus changes. In various embodiments, the force applied by the springs 120 is in the range of approximately 0.05 to 1.0 lbf, and in an embodiment, the force applied is approximately 0.25 lbf.

One end of the compression spring 120 abuts the ring 107, and the ring 107 thus acts as a support for the spring. The end of the spring opposite the ring 107 sits in a cup 130 that is rigid. The cup 130 may be made of molded plastic, polysulfone, titanium, stainless steel, or any other material that provides sufficient support for the spring 120. The cup 130 provides a rigid and smooth surface against which the spring 120 may act, in order to evenly distribute the substantially constant force on the fundus.

The cup 130 includes a cylindrical portion that passes through a cylindrical portion in the ring 107. The cylindrical portion of the ring 107 is sealed by a plug 134. The cylindrical portion of the cup 130 includes a tab 132 that abuts the cylindrical portion of the ring 107 when the spring has extended to its maximum extension, to prevent the lobe from extending too far to the center of the band 105 and into the fundus.

The lobe 115 is sealed from the patient's body and from contaminants with a flexible rolling diaphragm 125. As the spring 120 moves the cup 130 toward and away from the fundus, the diaphragm 125 flexes and moves with the cup. The diaphragm 125 is attached to the ring 107 via an interference fit between a diaphragm lip 126 and an interference portion 127 in the ring 107. FIG. 1E illustrates several lobes 115 with the rolling diaphragms 125 in place, whereas one lobe 115 has the diaphragm 125 removed to show the cup 130 underneath.

Figure 2:
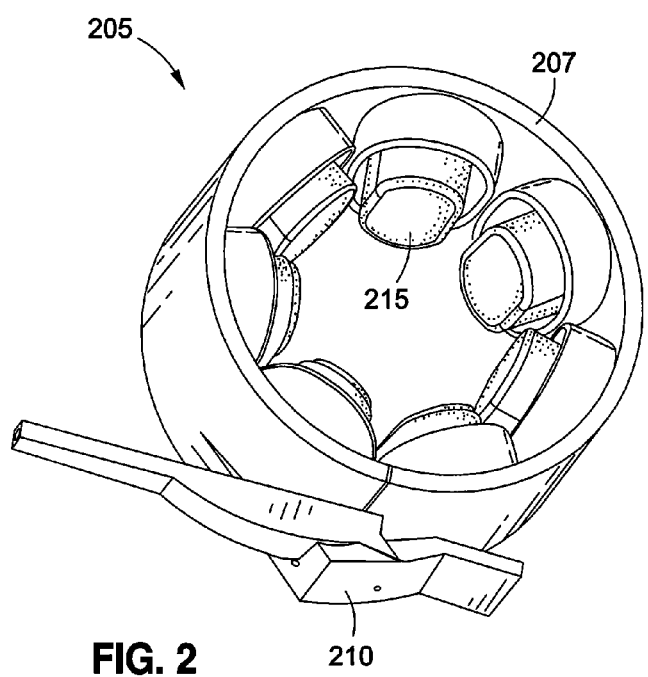
FIG. 2 illustrates a perspective view of a self-adjusting gastric band with oval-shaped lobes according to an embodiment of the present invention.

In various embodiments, more lobes 115 may be used to more equally distribute the substantially constant force about the fundus. For example, with reference to FIG. 2, a gastric band 205 includes seven oval-shaped lobes 215 to more equally distribute the force. Gastric band 205 also has a ring 207 and a latch mechanism 210.

With reference to FIGS. 3A-3D, another embodiment of a mechanically, self-adjustable gastric band 305 is disclosed. The band 305 is a handcuff-type design, with a hinge 308 rotatably coupling portions of the ring 307 to each other. Although only two portions of the ring 307 are illustrated, any number of portions and hinges 308 may be utilized to facilitate securing the band 305 to the fundus 300. A latch mechanism comprises a male portion 310 and a female portion 311 that secures the band 305 around a patient's fundus 300 (shown in broken lines as a cylinder for illustration purposes only).

The band 305 includes movable members that are vertically shaped cups 325 circumferentially disposed around the inside of the ring 307. The cups 325 automatically move into and out of the band to adapt to changes in the fundus 300 in order to apply a substantially constant force to the fundus 300. The cups 325 and/or other portions of the band 305 may be made of a low coefficient of friction material to reduce friction as the parts move with respect to each other. For example, various components may be made of silicone.

The cups 325 are biased against a back support 327 in the ring 307 with a torsional spring 320. The torsional spring 320 is coupled to the ring 307 via a roller 330 that passes through the center cylindrical portion of the spring 320. The roller 330 is rotationally and/or fixedly attached to the ring 307 via a roller pin 332 that passes through the roller 330. Thus, the roller 330 and center portion of the torsional spring 320 remain substantially stationary as the cups 325 move into and out of the band 305.

The ends of the torsional spring 320 are held by a spring holder 315 that is attached to the cup 325. The ends of the torsional spring 320 press against the back support 327 to provide a substantially constant force to the cup 325 against changes in size of the fundus 300. The cup 325 has slots that engage with the roller 330 and/or the roller pin 332 to provide a gimbal-pivoted support interaction between the spring 320 and the cup 325.

Figure 3A:
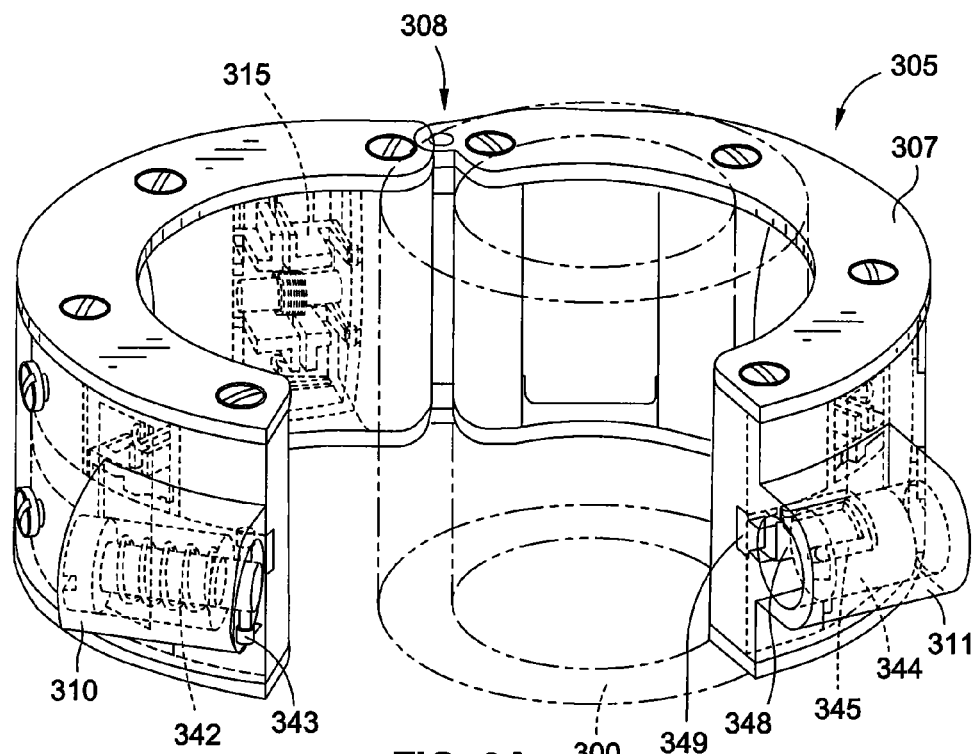
FIG. 3A illustrates a perspective view of a hinged, self-adjusting gastric band with a latch mechanism and vertical portions for applying a constriction to the fundus according to an embodiment of the present invention.
Figure 3B:
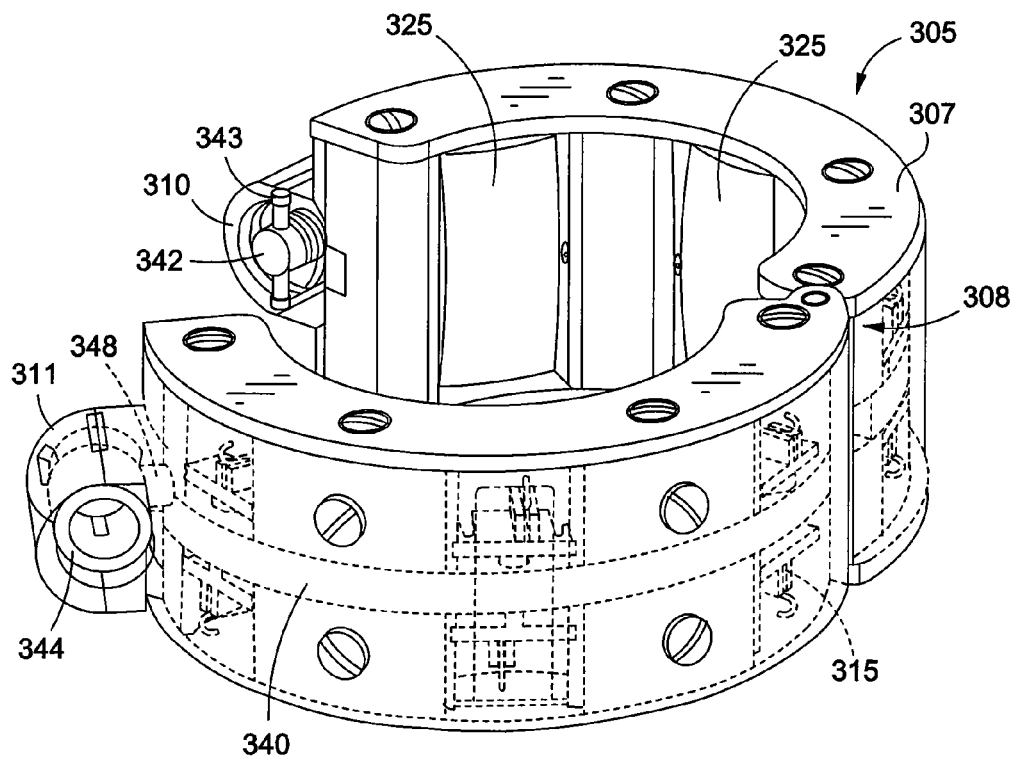
FIG. 3B illustrates another perspective view of the self-adjusting gastric band of FIG. 3A.
Figure 3C:
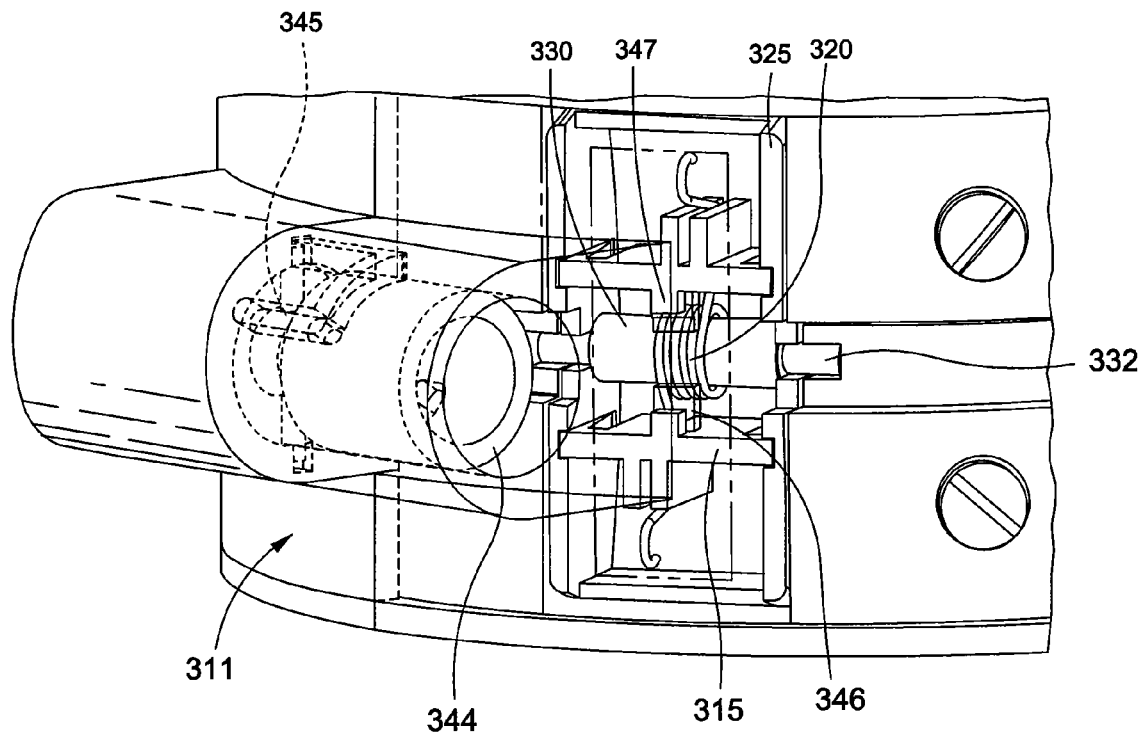
FIG. 3C illustrates a perspective, cut-away view of a spring holder and torsional spring of the self-adjusting gastric band of FIG. 3A.
Figure 3D:
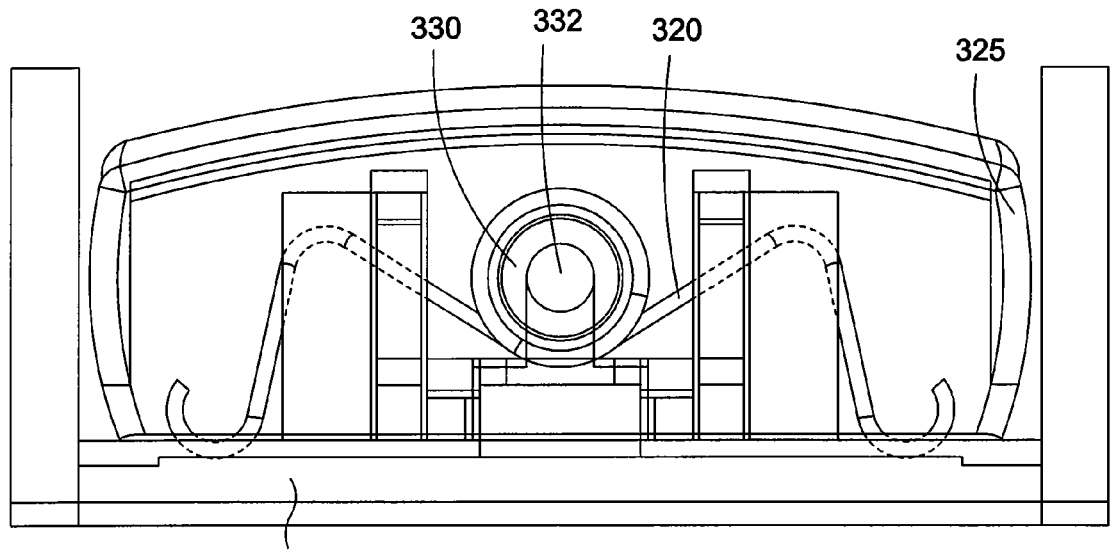
FIG. 3D illustrates a side, cut-away view of a vertical cup and torsional spring of the self-adjusting gastric band of FIG. 3A.

As illustrated in FIG. 3D, the cup 325 is pushed all the way into the band 305, and the roller pin 332 sits all the way to one end of the slot in the cup 325. In this manner, the ends of the torsional spring 320 are pushed away from the center of the torsional spring 320. As the cup 325 moves towards the fundus 300, the ends of the spring 320 tend to come together, resulting in a smaller moment arm.

With the moment arm of the spring 320 decreasing as the spring 320 moves towards a relaxed position and increasing as the spring 320 moves towards a wound position, the greater moment arm compensates for a potential increase in force as the spring 320 becomes more wound—as the cup 325 is pushed towards the back support 327. Thus, the spring 320 may exert a substantially constant force against the cup 325, which allows the cup 325 to exert a substantially constant force against the fundus 300. Further, the spring 320 may be preloaded to such a degree that small changes in deflection of the spring 320 result in a substantially constant force.

The male 310 and female 311 portions of the latch mechanism facilitate securing the band 305 around the fundus 300. The male portion 310 includes a cam screw 342 that is biased away from the female portion 311 with a compression spring. A physician uses an instrument such as a screw driver to push the cam screw 342 into the female portion 311 in order to secure the male portion 310 to the female portion 311 and in order to release the vertical cups 325 so they can exert a substantially constant force against the fundus 300.

A retaining ring 340 is circumferentially located around the band 305 and slides within the band 305 in order to release the vertical cups 325. The spring holder 315 attached to the vertical cup 325 includes a spring holder tab 347 that allows a retaining ring tab 346 to hold the spring holder 315 and the vertical cup 325 against the back support 327 in order to preload the spring 320. The retaining ring 340 also facilitates implanting the band 305 around the fundus 300 because the vertical cups 325 in the preloaded position are not exposed (which could lead to undesirable contact with the fundus 300 if they were exposed) as the band 305 is implanted.

FIGS. 3C and 3D illustrate the vertical cup 325 in this preloaded position, with the retaining ring tab 346 holding the spring holder tab 347 in place according to an embodiment of the present invention. In order to release the vertical cup 325, the retaining ring 340 rotates with respect to the vertical cup 325, and the retaining ring tab 346 slides away from the spring holder tab 347. The roller 330 may then slide within the vertical cup 325 as the spring 320 pushes the vertical cup 325 away from the back support 327.

In accordance with an embodiment, a ring release cylinder 344 is configured to facilitate sliding the retaining ring 340 within the band 305 in order to slide the retaining ring tabs 346 away from the spring holder tabs 347. The ring release cylinder 344 includes a cylinder tab 348 that abuts a retaining ring release tab 349 on the retaining ring 340 in order to rotate the retaining ring 340 as the cylinder 344 slides within the female portion 311 of the latch mechanism.

The cam screw 342 causes the cylinder 344 to slide within the female portion 311 when a physician inserts the cam screw 342 into the female portion 311. The cam screw 342 includes pins 343 at the end of the cam screw 342 closest to the female portion 311. These pins 343 are configured to slide within the pin slots 345 in the cylinder 344 as the physician pushes the cam screw 342 into the female portion 311.

When the pins 343 press against the cylinder 344 at the ends of the slots 345, the cylinder 344 slides within the female portion 311 and moves the cylinder tab 348. As the cylinder tab 348 moves, it pushes the retaining ring release tab 349 in order to rotate the retaining ring 340 with respect to the band 305. After the retaining ring 340 has been rotated to release the vertical cups 325, the physician rotates the cam screw 342 in the cylinder pin slots 345 in order to lock the cam screw 342 in the female portion 311 to secure the male portion 310 to the female portion 311 and to facilitate securing the band 305 about the fundus 300. The cam screw 342 and the cylinder 344 may also be used to reposition the retaining ring 340 to hold the spring holders 315 against the back supports 327 by moving the cylinder 344 in the direction opposite the direction discussed above.

Figure 4A:
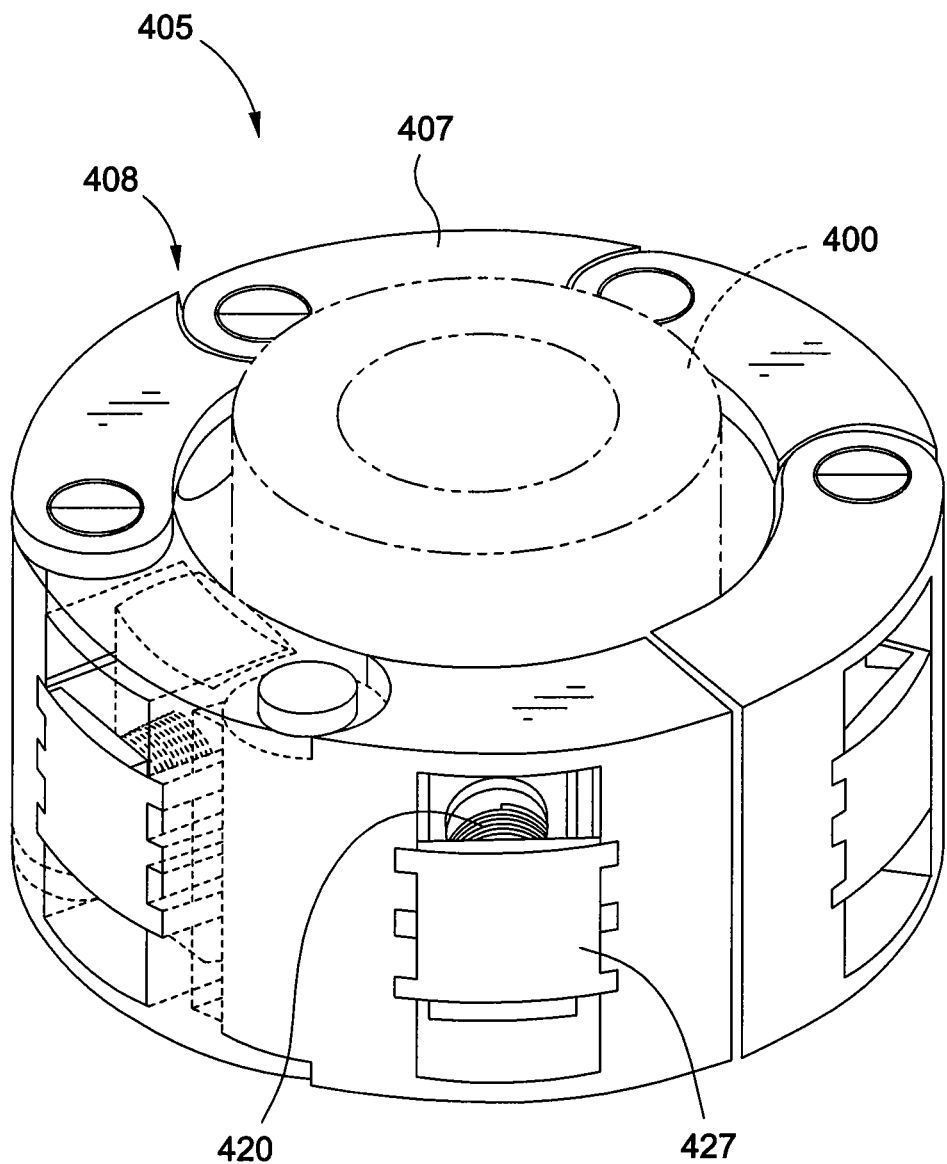
FIG. 4A illustrates a perspective view of a hinged, self-adjusting gastric band with a compression spring according to an embodiment of the present invention.
Figure 4B:
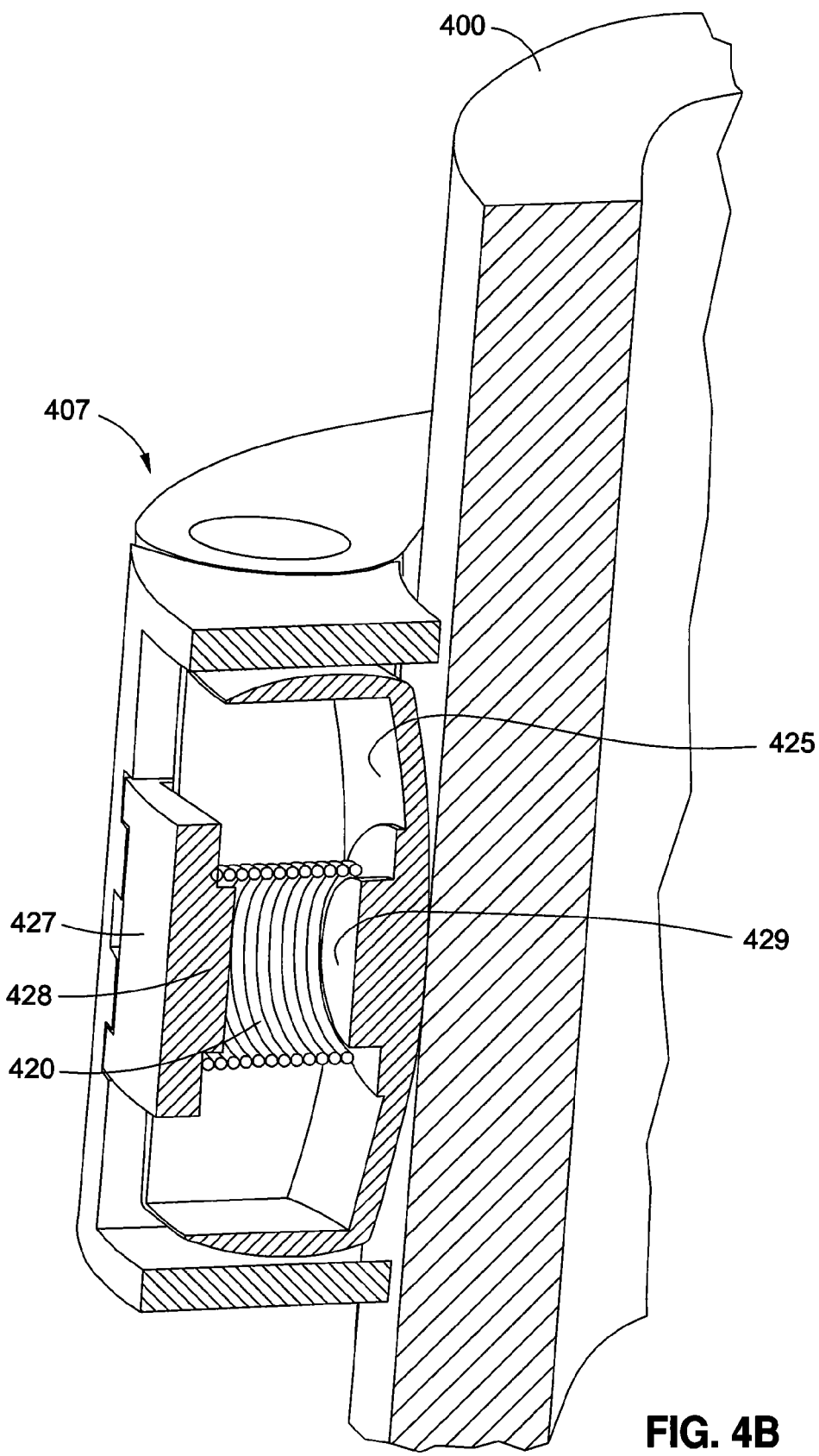
FIG. 4B illustrates a sectional view of a vertical cup and a compression spring of the self-adjusting gastric band of FIG. 4A.
Figure 5A:
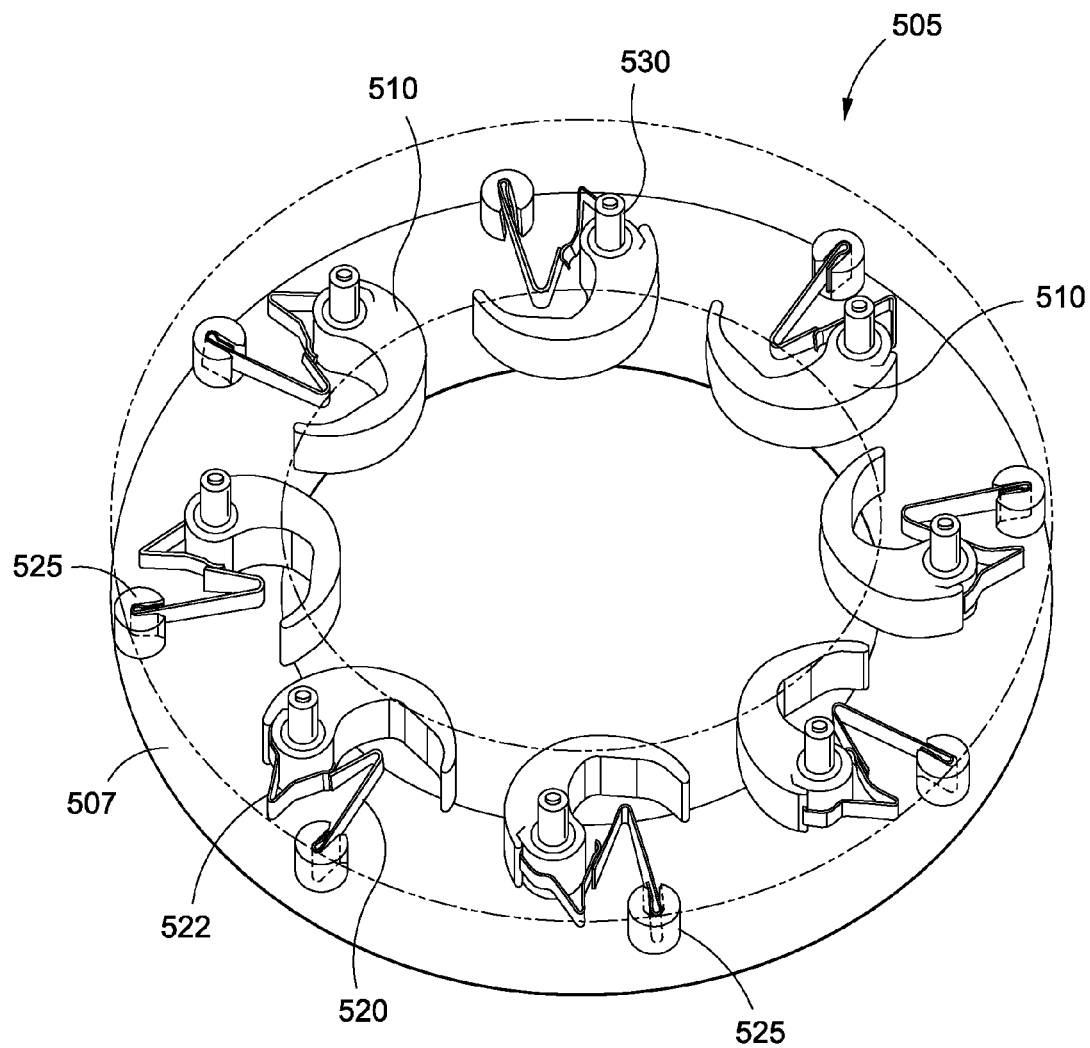
FIG. 5A illustrates a perspective view of a representation of a self-adjusting gastric band with movable fingers and dual leaf springs according to an embodiment of the present invention.
Figure 5B:
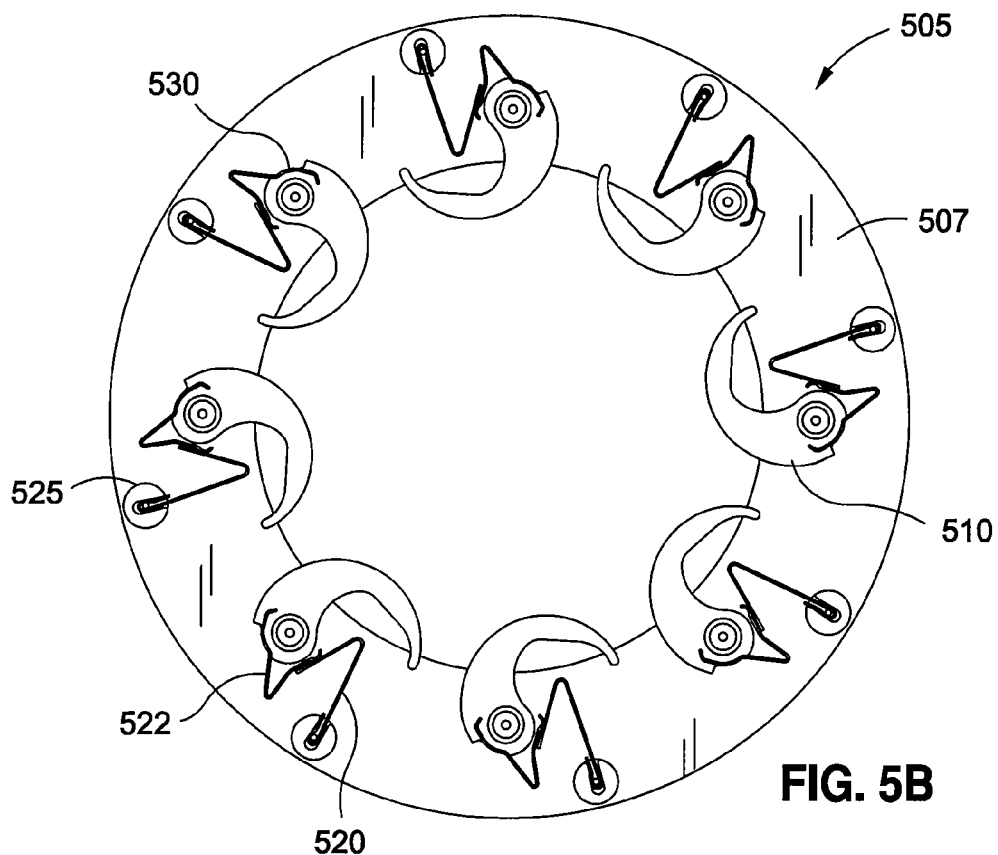
FIG. 5B illustrates a top view of the representation of the self-adjusting gastric band of FIG. 5A.

In another embodiment, as illustrated in FIGS. 4A-4B, a low-k compression spring 420 exerts a substantially constant force against a vertical cup 425 and a fundus 400. The vertical cups 425 are spaced circumferentially about a ring 407 of a self-adjusting gastric band 405. The ring 407 includes multiple hinges 408 to facilitate securing the band 405 to the fundus. Although five portions of the ring 407 and corresponding hinges 408 are illustrated, any number of portions and hinges 408 may be utilized to facilitate securing the band 405 to the fundus 400.

Similar to the embodiments illustrated in FIGS. 3A-3D, the self-adjusting band 405 may include a latch mechanism to close the band 405 and a retaining ring to facilitate releasing the vertical cups 425 from a preloaded position against a back support 427. But in some embodiments, a retaining ring or other release mechanism may not be used.

The compression spring 420 is coupled to the back support 427 via a back support spring retaining portion 428, and the spring 420 is coupled to the vertical cup 425 via a cup spring retaining portion 429 opposite the back support 427. The compression spring 420 may be similar to the spring 120 discussed above with respect to FIGS. 1A-1E in that the movement of the spring 420 and the vertical cup 425 are small with respect to the uncompressed length of the spring 420. Thus, the spring 420 exhibits a substantially constant force over its range of motion in the self-adjusting band 405.

In accordance with various embodiments, and with reference to FIGS. 5A-5D, rotatable fingers 510 may be utilized to provided a desired constriction of the patient's fundus. FIGS. 5A-5D illustrate the functionality of the fingers 510, but the ring 507 upon which the fingers 510 are disposed is only representative of a ring 507 of a self-adjusting gastric band 505. It should be understood that variations to the structure of the ring 507 to facilitate securing the ring 507 about the fundus are contemplated within the scope of the present disclosure.

The rotatable fingers 510 are rotatably coupled to the ring 507 at pivots 530. When the rotatable fingers 510 rotate counter-clockwise, they increase the constriction of the fundus by rotating toward the center of the ring 507. When the rotatable fingers 510 rotate clockwise, they decrease the constriction of the fundus by rotating away from the center of the ring 507.

A first leaf spring 520 is coupled to the ring 507 via a spring holder 525. A second leaf spring 522 is coupled to the rotatable finger 510, and the free ends of the leaf springs 520, 522 overlap. In this manner, the two leaf springs 520, 522 bias the rotatable finger 510 toward the center of the ring 507 and toward the fundus with a substantially constant force.

The leaf springs 520, 522 are preloaded to generate the desired force. In an embodiment, the desired force is in the range of approximately 0.1 to approximately 1.0 lbf. Further in an embodiment, the desired force is approximately 0.25 lbf. The range of angular motion of the leaf springs may normally produce small variations in the spring force, but the force remains substantially constant in an embodiment because the increase in a lever arm of the stationary leaf spring 520 causes an effective reduction of the spring factor and therefore a substantially constant resultant force.

In various embodiments, any mechanism for reducing the spring factor while increasing the deflection results in a substantially constant force applied to the fingers 510, and all such mechanisms are contemplated within the scope of the present invention. In another embodiment, the leaf springs and fingers may be configured such that the same deflection and lever arm result regardless of the rotation angle in order to obtain a substantially constant force.

The leaf spring 522 that rotates with the finger 510 is also configured to result in a substantially constant force as the finger 510 rotates. The resultant force works through lever arms of both springs 520, 522, so the geometry of the springs 520, 522 is configured to produce the desired resultant force. Further, based on the geometry of the springs 520, 522 and/or the fingers 510, any desired force profile may be developed by a combination of springs and lever arms. For example, in an embodiment, it may be desirable for the force applied to the fundus to increase or decrease as the fundus geometry changes to provide physiological benefits.

Figure 6:
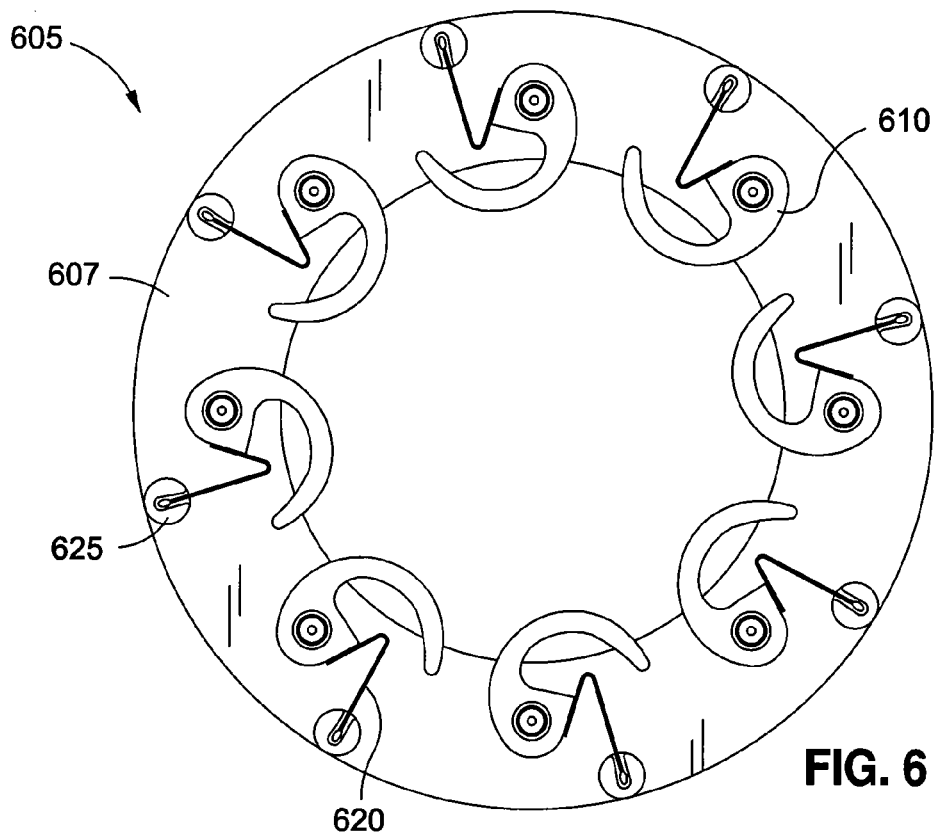
FIG. 6 illustrates a perspective view of another representation of a self-adjusting gastric band with leaf springs coupled to movable fingers according to an embodiment of the present invention.
Figure 5C:
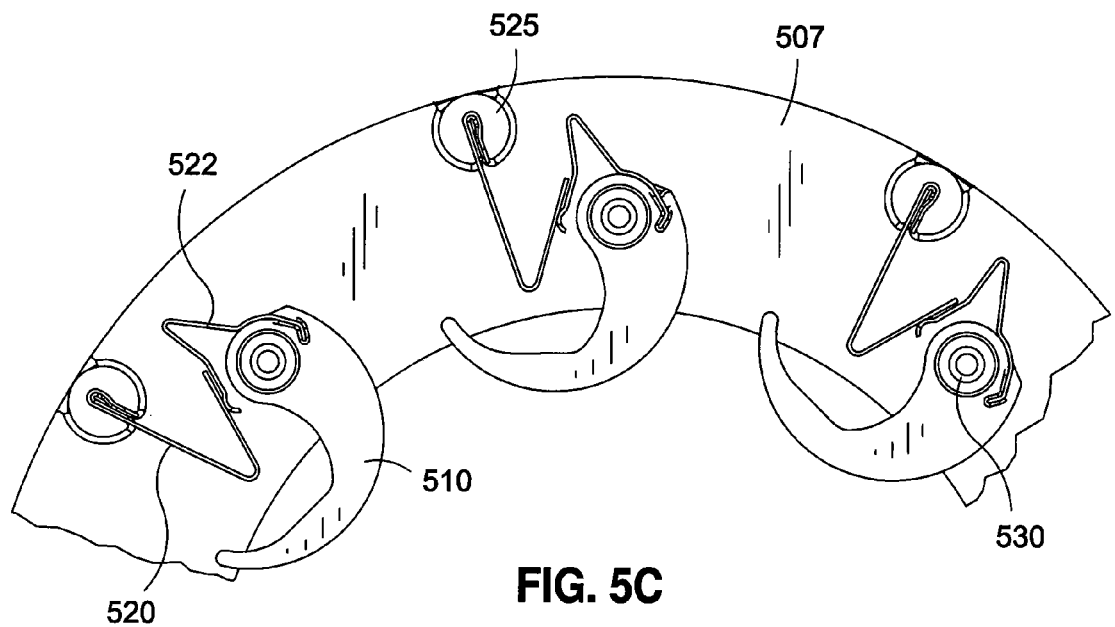
FIG. 5C illustrates a partial view of the representation of the self-adjusting gastric band of FIG. 5A.
Figure 5D:
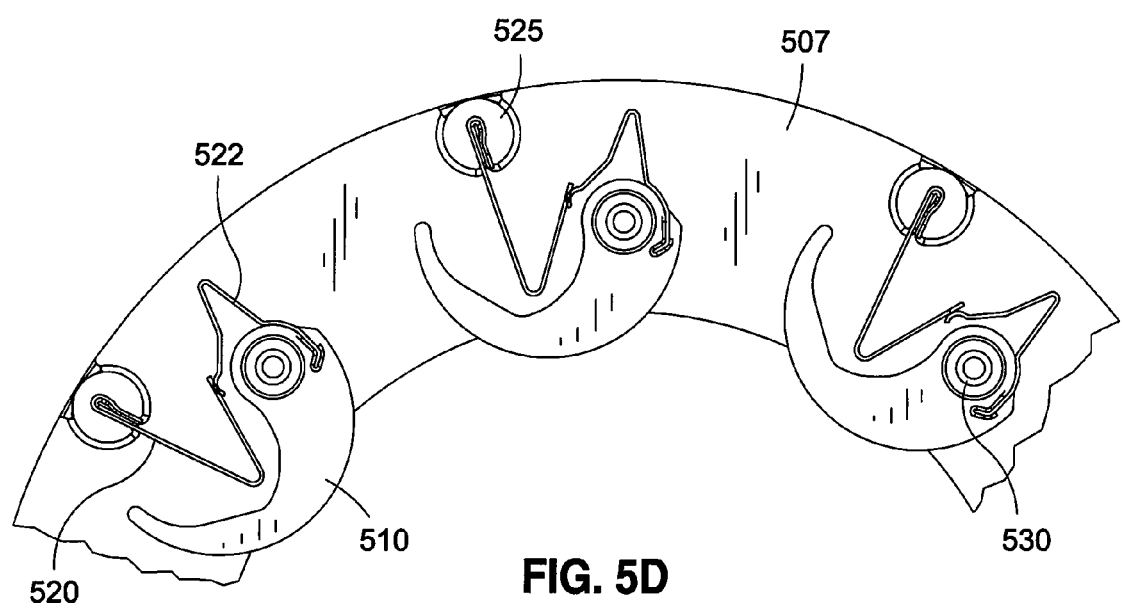
FIG. 5D illustrates another partial view of the representation of the self-adjusting gastric band of FIG. 5A.

In an embodiment, and with reference to FIG. 6, one leaf spring 620, coupled to the ring 607 via a spring holder 625, may be used to provide the desired force to a rotatable finger 610. The spring 620 may slide along one edge of the finger 610 as the finger 610 rotates, thereby changing the effective lever arm of the spring 620. When the lever arm increases as the deflection increases, the resultant force applied to the finger 610 remains substantially constant.

In various embodiments, and with reference to FIGS. 7A-7G, a gastric band 705 includes a canted spring 720 to provide a substantially constant force to a plurality of lobes 715 in order to achieve a desired constriction to a patient's fundus. The lobes 715 may be made of silicone rubber of a low durometer so that the lobes 715 are compliant and flex with movement of the fundus. For example, the lobes 715 may apply more or less of a constriction to the fundus to allow for a large bolus to pass through the fundus or to accommodate changes in size, shape, and/or location of the fundus. In an embodiment, the outer shell or ring 707 may be made of a higher durometer silicone rubber than the lobes 715. A latch 710 may be used to secure the band 705 around the patient's fundus.

The canted spring 720 is circumferentially disposed around the band 705. The outside diameter of the canted spring 720 is configured to abut the ring 707 of the gastric band 705, and the inside diameter of the spring 720 is configured to abut the lobes 715. In an embodiment, the lobes 715 may be a continuous, flexible component. The canted spring 720 deflects radially in response to changes in the size, shape, and/or position of the fundus. The radial deflection of the spring 720 causes the inside diameter of the band 705 to change as the lobes 715 move in and out. As the canted spring 720 deflects, it applies a substantially constant force against the lobes 715 and the fundus. The substantially constant force is maintained because the effective lever arm of the spring 720 increases as the deflection increases.

Figure 7A:
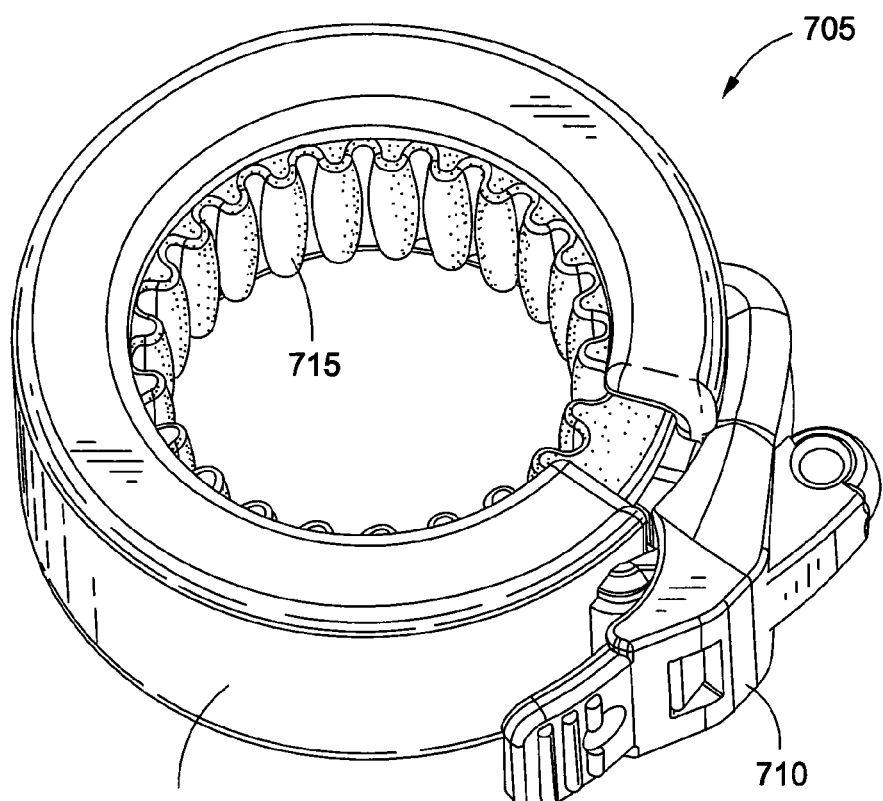
FIG. 7A illustrates a perspective view of a self-adjusting mechanical gastric band according to an embodiment of the present invention.
Figure 7B:
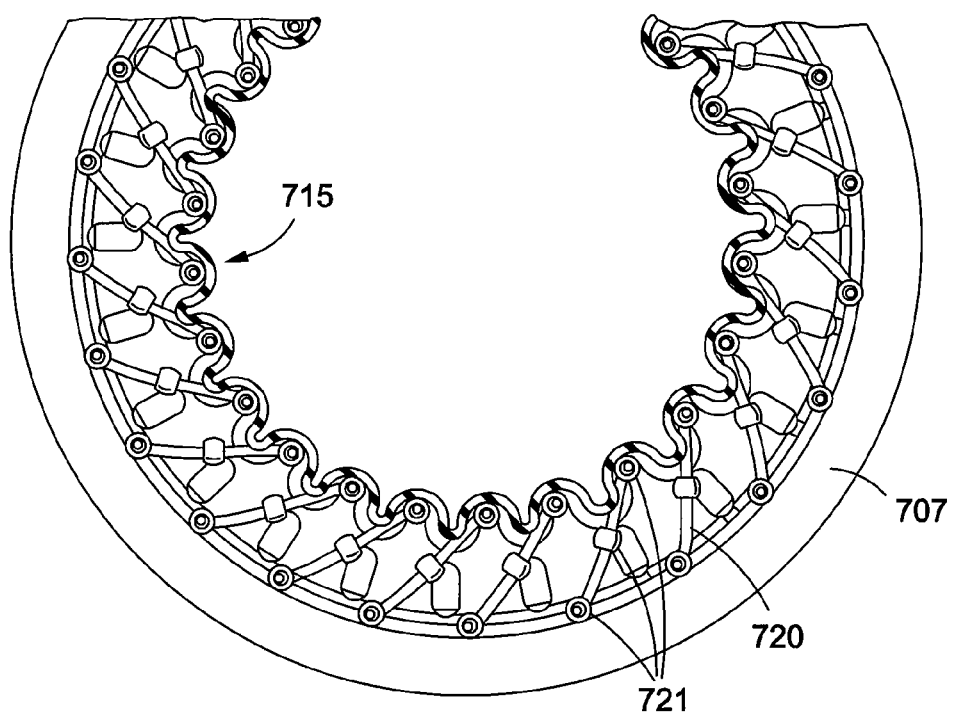
FIG. 7B illustrates a partial cut-away view of a canted spring in the self-adjusting mechanical gastric band of FIG. 7A.
Figure 7C:
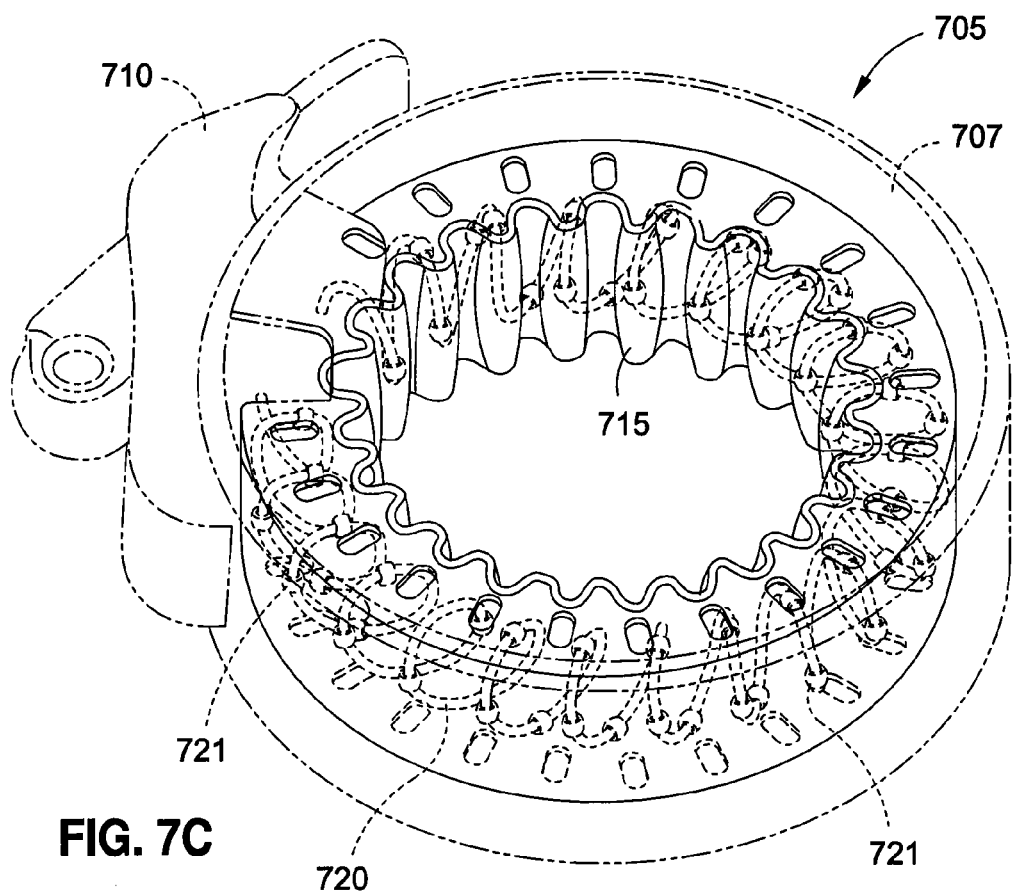
FIG. 7C illustrates a perspective wire frame view of the self-adjusting mechanical gastric band of FIG. 7A.
Figure 7D:
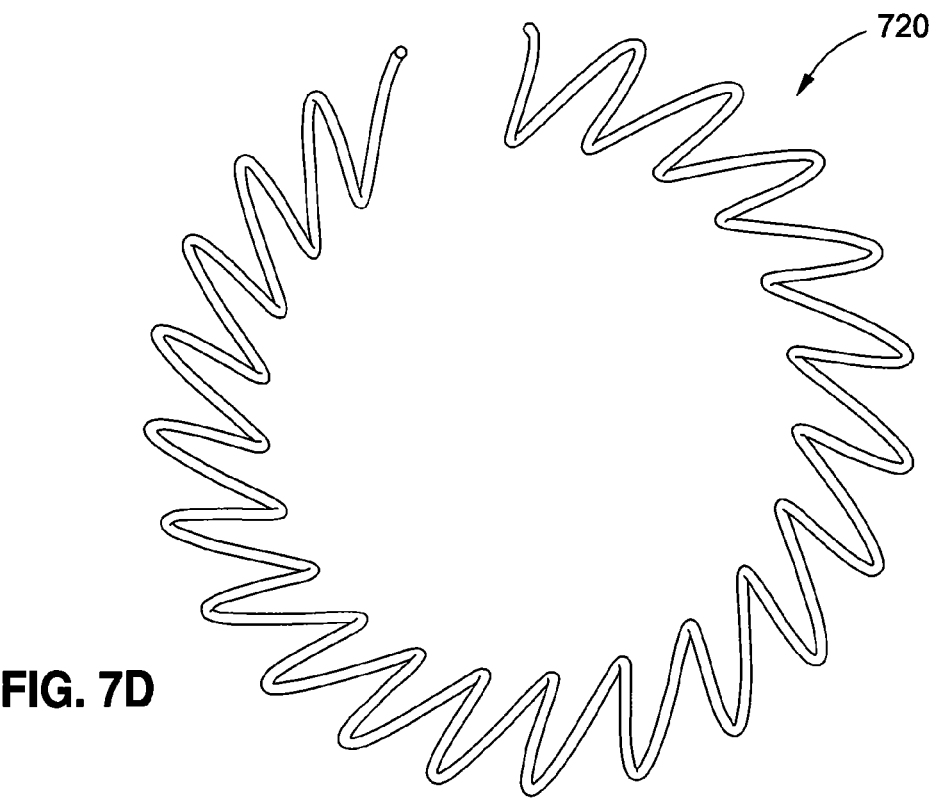
FIG. 7D illustrates a perspective view of a canted spring according to an embodiment of the present invention.
Figure 7E:
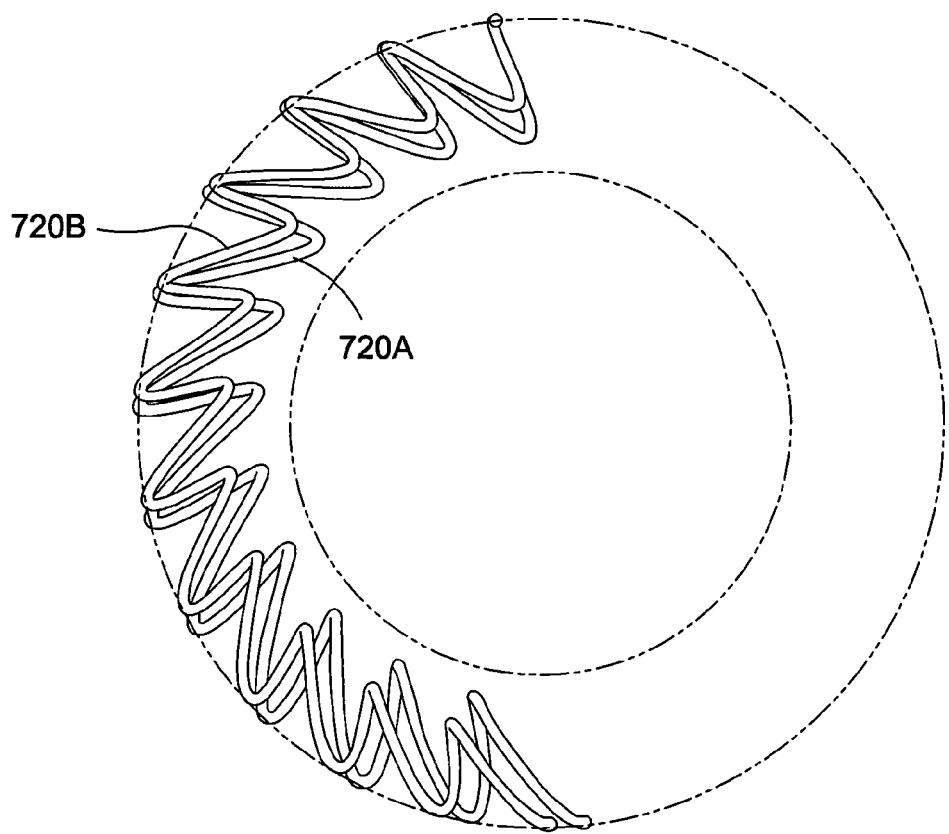
FIG. 7E illustrates a perspective view of a canted spring in two states of deflection according to an embodiment of the present invention.
Figure 7F:
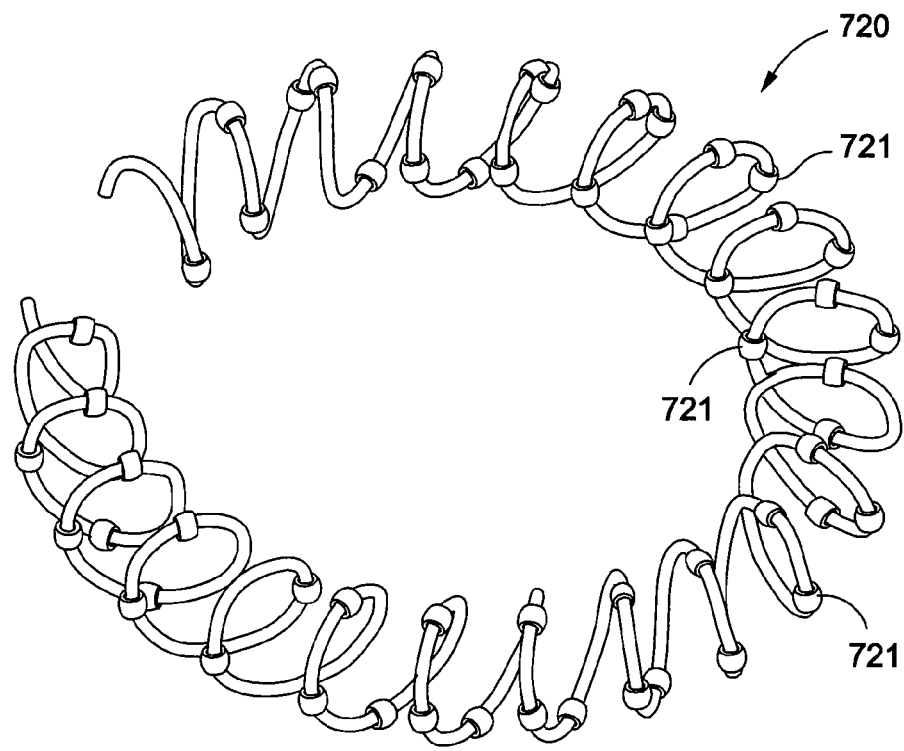
FIG. 7F illustrates a perspective view of a canted spring with rollers according to an embodiment of the present invention.

In accordance with an embodiment, with reference particularly to FIG. 7E, the canted spring 720 is illustrated at a first degree of deflection 720A and a second degree of deflection 720B. The first degree of deflection 720A results in a smaller inside diameter formed by the lobes 715, while the second degree of deflection 720B results in a larger inside diameter formed by the lobes 715. The spring 720 provides a substantially constant radial force at both the first and the second degrees of deflection. It should be understood that the canted spring 720, as with the other springs disclosed herein, may have various deflected positions, and two are shown here for purposes of illustration only, and not by way of limitation.

The canted spring 720 may include various mechanisms and/or characteristics to reduce friction between the coils of the spring 720, the lobes 715, the ring 707 and/or other portions of the gastric band 705. For example, rollers 721 may be placed along the spring 720 to facilitate reducing friction with the silicone material of the band 705 (e.g., the lobes 715 and/or the ring 707) as the spring 720 deflects. The rollers 721 may be located at various locations on the spring 720, and in an embodiment, the rollers 721 may cover substantially the entire spring 720. In other embodiments, silicone oil or another lubricating material may be utilized to reduce friction. Further, a low-friction silicone may be utilized as a laminating layer for the spring 720 to reduce friction.

Figure 7G:
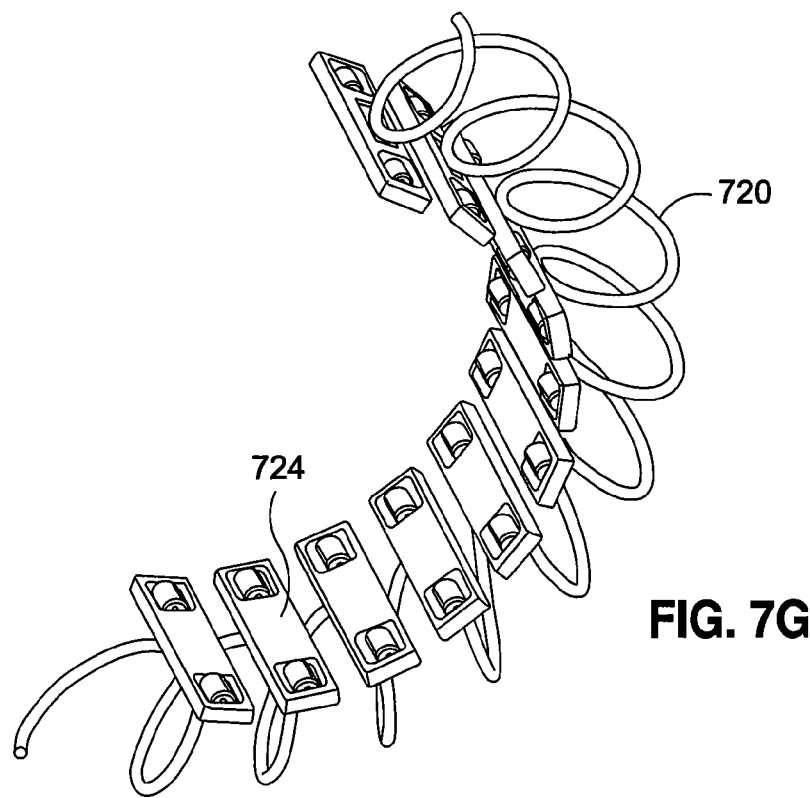
FIG. 7G illustrates a perspective view of a canted spring with wheel carts according to an embodiment of the present invention.

In accordance with another embodiment, and with reference to FIG. 7G, wheel carts 724 may be utilized to reduce friction between the spring 720 and the components of the band 705. The wheel carts 724 may be disposed between the spring 720 and the lobes 715, the ring 707, and/or other components of the band 705. In an embodiment, the wheel carts 724 are coupled to the spring 720, and the wheel carts 724 slide along the surface of the band 705 that they contact as the spring 720 deflects.

Figure 8:
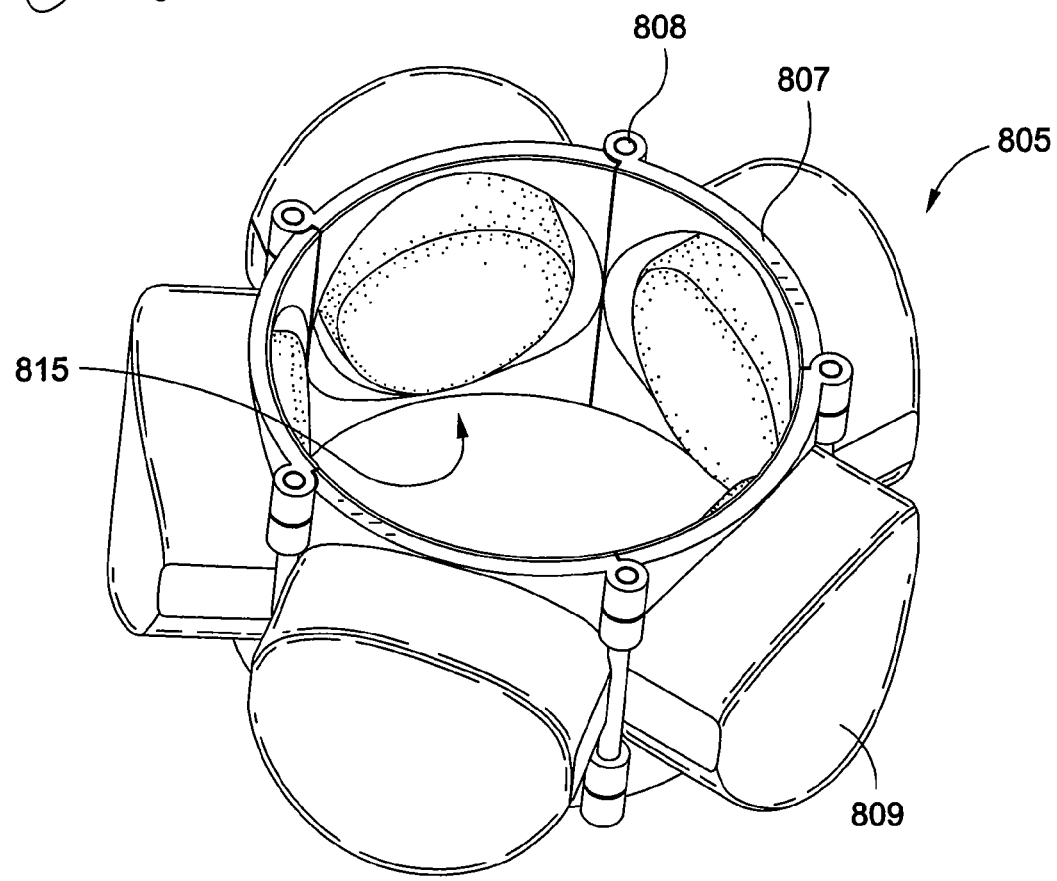
FIG. 8 illustrates a perspective view of a hinged self-adjusting gastric band according to an embodiment of the present invention.

With reference to FIG. 8, a self-adjusting gastric band 805, according to an embodiment, includes hinges 808 that define segments of a ring 807 of the gastric band 805. The hinges allow the segments of the ring 807 to move in order to facilitate implantation of the band 805. Further, the hinged segments are modular which facilitates simpler fabrication and/or molding of the segments of the band 805.

Each segment includes an outer cup portion 809 configured to receive a near-constant force compression spring. The near-constant force compression spring abuts the outer cup portion 809 on one end, and a lobe 815 on the other end. The structure of the lobe 815 and the near-constant force compression spring are similar to the embodiments illustrated in FIGS. 1A-1E and FIG. 2. The near-constant force compression spring expands and contracts with changes in the patient's fundus, to facilitate automatically self-adjusting to the changes and applying a substantially constant force to the fundus.

Unless otherwise indicated, all numbers expressing quantities of ingredients, components, forces, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of and/or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A mechanically self-adjusting, gastric band, which when banded assumes a ring configuration, the band constructed to be banded about a fundus, the self-adjusting gastric band comprising:
   a movable member, moveable in a radial direction when the band is in the ring configuration, for contacting the fundus; and
   a spring biasing member for applying a substantially constant force in a radially inward direction to the moveable member, the biasing member automatically moving the movable member in the radially inward direction relative to the ring configuration, wherein the movable member self-adjusts radially in response to the biasing force applied by the spring biasing member as the fundus adjusts in size.

2. The self-adjusting gastric band of claim 1, wherein when the fundus increases in size as a large bolus enters the fundus, the movable member self-adjusts radially to a second position from an initial position in response to the biasing force applied by the spring biasing member and when the large bolus passes through the fundus, the moveable member self-adjusts radially to the initial position, wherein the movable member has substantially the same stiffness at the initial position and the second position.

3. The self-adjusting gastric band of claim 1, wherein a constriction formed by the band when the moveable member is at the first position is looser than a constriction formed by the band when the moveable member is at the second position.

4. The self-adjusting gastric band of claim 1, wherein the substantially constant force is in the range of about 0.05 to about 1.0 lbf.

5. The self-adjusting gastric band of claim 1, wherein the substantially constant force is about 0.25 lbf.

6. The self-adjusting gastric band of claim 1, wherein the movable member is a lobe comprising a rolling diaphragm extending from a surface of the self-adjusting gastric band.

7. The self-adjusting gastric band of claim 6, further comprising up to seven lobes.

8. The self-adjusting gastric band of claim 6, wherein the biasing mechanism is a near-constant force compression spring disposed within a cup proximate the rolling diaphragm, wherein the near-constant force compression spring abuts the surface of the band to facilitate moving the rolling diaphragm to impose a constriction.

9. The self-adjusting gastric band of claim 8, wherein the cup comprises a tab to prevent the near-constant force compression spring from expanding beyond a predetermined distance.

10. The self-adjusting gastric band of claim 1, wherein the movable member is a cup slidably coupled to a roller that is coupled to a ring of the self-adjusting gastric band.

11. The self-adjusting gastric band of claim 10, wherein the spring biasing member is a torsional spring coupled to the roller, and the torsional spring comprises ends that contact a back support of the ring to facilitate applying the substantially constant force to the movable member.

12. The self-adjusting gastric band of claim 11, wherein the cup slides toward the back support when a bolus enters the fundus.

13. The self-adjusting gastric band of claim 12, wherein a moment arm of the torsional spring increases as the cup slides toward the back support, wherein the increased moment arm facilitates maintaining the substantially constant force.

14. The self-adjusting gastric band of claim 12, further comprising a retaining ring circumferentially disposed about the self-adjusting gastric band, the retaining ring comprising a release tab abutting a tab on the spring holder for maintaining the spring holder in a preloaded position against the back support, and when the retaining ring rotates around the self-adjusting gastric band, the release tab slides past the spring holder tab to release the spring holder and the cup to facilitate the cup exerting the substantially constant force on the movable member.

15. The self-adjusting gastric band of claim 14, further comprising a latch mechanism having a male portion and a female portion, the male portion comprising a cam screw and the female portion comprising a slidable cylinder.

16. The self-adjusting gastric band of claim 15, wherein the cam screw comprises pins and the slidable cylinder comprises pin slots for receiving the pins when the cam screw is inserted into the slidable cylinder.

17. The self-adjusting gastric band of claim 16, wherein the slidable cylinder comprises a tab that abuts a retaining ring release tab on the retaining ring, wherein the cylinder tab pushes the retaining ring release tab to rotate the retaining ring when the cam screw is inserted into the slidable cylinder and slides the slidable cylinder within the female portion, the retaining ring releasing the cup as the retaining ring rotates.

18. The self-adjusting gastric band of claim 17, wherein the cam screw secures the male portion to the female portion to secure the self-adjusting band gastric band around the fundus when the cam screw rotates within the pin slots after rotating the retaining ring.

19. The self-adjusting gastric band of claim 1, wherein the movable member is a vertical cup disposed circumferentially about the self-adjusting gastric band, and wherein the spring biasing member is a compression spring coupled to a back support on a ring of the self-adjusting gastric band, the compression spring providing the substantially constant force against the cup and the fundus.

20. The self-adjusting gastric band of claim 19, further comprising a retaining ring circumferentially disposed around the self-adjusting gastric band to release the cup from a preloaded position against the back support when the retaining ring rotates with respect to the self-adjusting gastric band.

21. The self-adjusting gastric band of claim 2, wherein the movable member is a rotatable finger coupled to a pivot on a ring of the self-adjusting gastric band, the rotatable finger rotating counter-clockwise to apply the first constriction and rotating clockwise to apply the second constriction in response to the large bolus entering the fundus.

22. The self-adjusting gastric band of claim 21, wherein the spring biasing member is a leaf spring coupled to the ring, the leaf spring biasing the rotatable finger toward the fundus at the substantially constant force.

23. The self-adjusting gastric band of claim 22, wherein a lever arm of the leaf spring increases as the rotatable finger rotates to maintain the substantially constant force.

24. The self-adjusting gastric band of claim 22, further comprising a second leaf spring, the leaf spring and the second leaf spring biasing the rotatable finger toward the fundus.

25. The mechanically self-adjusting gastric band according to claim 1, wherein the movable member extends from an inner surface of the gastric band.

26. The mechanically self-adjusting gastric band according to claim 25, comprising a plurality of movable members, wherein when the gastric band is placed around the fundus, the movable members are disposed circumferentially around the inner surface of the gastric band.

27. The self-adjusting gastric band of claim 1, further comprising a plurality of the moveable members and a plurality of the spring biasing members, each biasing member corresponding to a moveable member.

28. A mechanically self-adjusting, gastric band, which when banded assumes a ring configuration in which the band has a radially inner surface and a radially outer surface, the band constructed to be banded about a fundus, the self-adjusting gastric band comprising:
   a lobe, extending from the radially inner surface and moveable in a radial direction when the band is in the ring configuration, for contacting the fundus, wherein the lobe includes
   i. a rolling diaphragm coupled to the radially inner surface of the band;
   ii. a cup disposed between the diaphragm and the radially inner surface of the band;
   iii. a near-constant force compression spring disposed within the cup and contacting the radially inner surface of the band, wherein the diaphragm, cup, and spring are constructed to move in a radial direction relative to the ring configuration, the spring constructed to apply a substantially constant force to the cup and the diaphragm, the near-constant force compression spring automatically moving the cup and the rolling diaphragm in the radial direction relative to the ring configuration, wherein the cup and the rolling diaphragm self-adjust radially in response to the biasing force applied by the spring as the fundus adjusts in size.

29. The mechanically self-adjusting gastric band according to claim 28, comprising a plurality of lobes, wherein when the gastric band is banded around the fundus in the ring configuration, the lobes are disposed circumferentially around the radially inner surface of the gastric band.

30. The gastric band of claim 28, further comprising a plurality of the lobes spaced circumferentially around the radially inner surface.

* * * * *